(12) United States Patent
Meergans et al.

(10) Patent No.: US 9,480,655 B2
(45) Date of Patent: Nov. 1, 2016

(54) SOLID PHARMACEUTICAL DOSAGE FORM OF DOLUTEGRAVIR

(71) Applicant: ratiopharm GmbH, Ulm (DE)

(72) Inventors: Dominique Meergans, Munich (DE); Sabine Prohl, Munich (DE); Hans Juergen Mika, Bonn (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/763,735

(22) PCT Filed: Feb. 18, 2014

(86) PCT No.: PCT/EP2014/053139
§ 371 (c)(1),
(2) Date: Jul. 27, 2015

(87) PCT Pub. No.: WO2014/125124
PCT Pub. Date: Aug. 21, 2014

(65) Prior Publication Data
US 2016/0030353 A1    Feb. 4, 2016

Related U.S. Application Data

(60) Provisional application No. 61/765,886, filed on Feb. 18, 2013, provisional application No. 61/847,718, filed on Jul. 18, 2013.

(30) Foreign Application Priority Data

Feb. 18, 2013  (EP) .................................. 13155649
Jul. 18, 2013  (EP) .................................. 13177084

(51) Int. Cl.
*A61K 9/20*     (2006.01)
*A61K 31/5365*  (2006.01)
*A61K 31/535*   (2006.01)
*A61K 9/16*     (2006.01)

(52) U.S. Cl.
CPC ........... *A61K 9/2009* (2013.01); *A61K 9/1682* (2013.01); *A61K 9/2077* (2013.01); *A61K 9/2095* (2013.01); *A61K 31/535* (2013.01); *A61K 31/5365* (2013.01)

(58) Field of Classification Search
CPC ..................................................... A61K 9/2009
USPC .............................................. 514/230, 230.2
See application file for complete search history.

(56) References Cited

U.S. PATENT DOCUMENTS

2011/0152303 A1    6/2011  Johns

FOREIGN PATENT DOCUMENTS

| WO | WO 2006/116764    | 11/2006 |
| WO | 2010/068253 A1 *  | 6/2010  |
| WO | WO 2011/094150    | 8/2011  |
| WO | WO 2012/151361    | 11/2012 |
| WO | WO 2013/038407    | 3/2013  |

OTHER PUBLICATIONS

Gopinath et al., J. Chem. Pharm. Sci. (2012), vol. 5(3), pp. 105-112.*
Chen, S. et al., *Pharmacotherapy 2012*, Pharmacotherapy Publications, Inc. USA (Apr. 2012), vol. 32, No. 4, pp. 333-339.

* cited by examiner

*Primary Examiner* — Taofiq A Solola
(74) *Attorney, Agent, or Firm* — Chalin A. Smith; Smith Patent LLC

(57) ABSTRACT

The present invention relates to a solid pharmaceutical dosage form comprising dolutegravir, a method of its preparation and its use in the treatment of an HIV infection.

10 Claims, 19 Drawing Sheets

SOLID PHARMACEUTICAL DOSAGE FORM OF DOLUTEGRAVIR

PRIORITY

This application corresponds to the U.S. national phase of International Application No. PCT/EP2014/053139, filed Feb. 18, 2014, which, in turn, claims priority to European Patent Application No. 13.155649.0 and U.S. Provisional Application No. 61/765,886, both filed Feb. 18, 2013, and European Patent Application No. 13.177084.4 and U.S. Provisional Application No. 61/847,718, both filed Jul. 18, 2013, the contents of which are incorporated by reference herein in their entirety.

FIELD OF THE INVENTION

The present invention relates to a solid pharmaceutical dosage form comprising dolutegravir, a method of its preparation and its use in the treatment of an HIV infection.

BACKGROUND OF THE INVENTION

Dolutegravir is the INN of (4R,12aS)-N-(2,4-difluorobenzyl)-7-hydroxy-4-methyl-6,8-dioxo-3,4,6,8,12,12a-hexahydro-2H-pyrido[1',2':4,5]pyrazino[2,1-b][1,3]oxazine-9-carboxamide which has the following chemical formula:

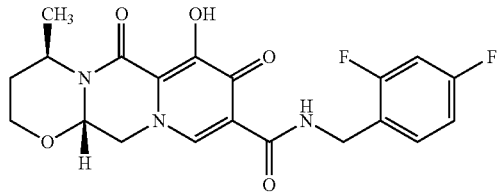 [SMILES: C[C@@H]1CCO[C@H]2Cn3cc(C(=O)NCc4ccc(F)cc4F)c(=O)c(O)c3C(=O)N12]

Dolutegravir is known from WO2006/116764 as a compound possessing an antiviral activity, in particular an inhibitory activity against HIV integrase. WO2006/116764 also discloses a tablet prepared using one among the many active ingredients disclosed in this document, microcrystalline cellulose, fumed silicon dioxide and stearic acid. The tablets are prepared by direct compression. WO2006/116764 further discloses a capsule filled with the active ingredient, starch as diluent and magnesium stearate as lubricant.

The sodium salt of dolutegravir and a specific crystalline form of this sodium salt or a hydrate thereof are disclosed in WO2010/068253.

Dolutegravir is practically insoluble and even the known sodium salt of dolutegravir is practically insoluble (solubility below 0.1 mg/ml) in 0.1 N HCl (pH 1.2). At an increasing pH, for example to pH 6.8 in 50 mM $KH_2PO_4$ the solubility of the sodium salt of dolutegravir slightly increases but the salt still remains very slightly soluble (1-0.1 mg/ml), only. Due to this very low solubility of the active ingredient the tablets known from WO2006/116764 are of little practical use because the active ingredient will hardly dissolve in the intestine resulting in a low bioavailability.

When repeating the preparation of the tablets disclosed in WO2006/116764, it was furthermore observed that different formulation batches showed differences between the dissolution rates. Additionally, serious difficulties were observed due to an insufficient flowability of dolutegravir and its distinct tendency to sticking. Another disadvantage is the very high volume of this active pharmaceutical ingredient.

Therefore, there is a need for improved solid pharmaceutical dosage forms comprising dolutegravir. In particular, there is a need for solid pharmaceutical dosage forms comprising dolutegravir showing increased dissolution rate of the active ingredient. Furthermore, there is a need for solid pharmaceutical dosage forms comprising dolutegravir which can be manufactured in a reliable and repeatable manner.

SUMMARY OF THE INVENTION

It has now surprisingly been found that the above and other problems may be solved by the addition of a compound comprising an alkaline earth metal ion and/or an alkaline compound to the composition. Furthermore, it was surprisingly found that manufacturing of the pharmaceutical dosage form by wet granulation results in dosage forms of reliable and repeatable dissolution profile.

The present invention therefore relates to a solid pharmaceutical dosage form comprising dolutegravir or a pharmaceutically acceptable salt or solvate thereof and a compound comprising an alkaline earth metal ion and/or an alkaline compound. The invention further relates to a solid pharmaceutical dosage form comprising dolutegravir or a pharmaceutically acceptable salt or solvate thereof which is obtainable by wet granulation.

Dolutegravir may be present in the solid pharmaceutical dosage form in its non-salt form or any pharmaceutically acceptable salt or solvate thereof. Suitable pharmaceutically acceptable salts are known to the skilled person. For example, dolutegravir may be present as alkali metal salt, such as dolutegravir sodium or dolutegravir potassium. The potassium salt being preferred. As it has been found that the potassium salt is surprisingly more soluble than the sodium salt of dolutegravir, the invention in an alternative embodiment is directed to the potassium salt of dolutegravir or a solvate thereof (independent of the pharmaceutical dosage form).

DETAILED DESCRIPTION OF THE PREFERRED EMBODIMENTS

Figure 1:
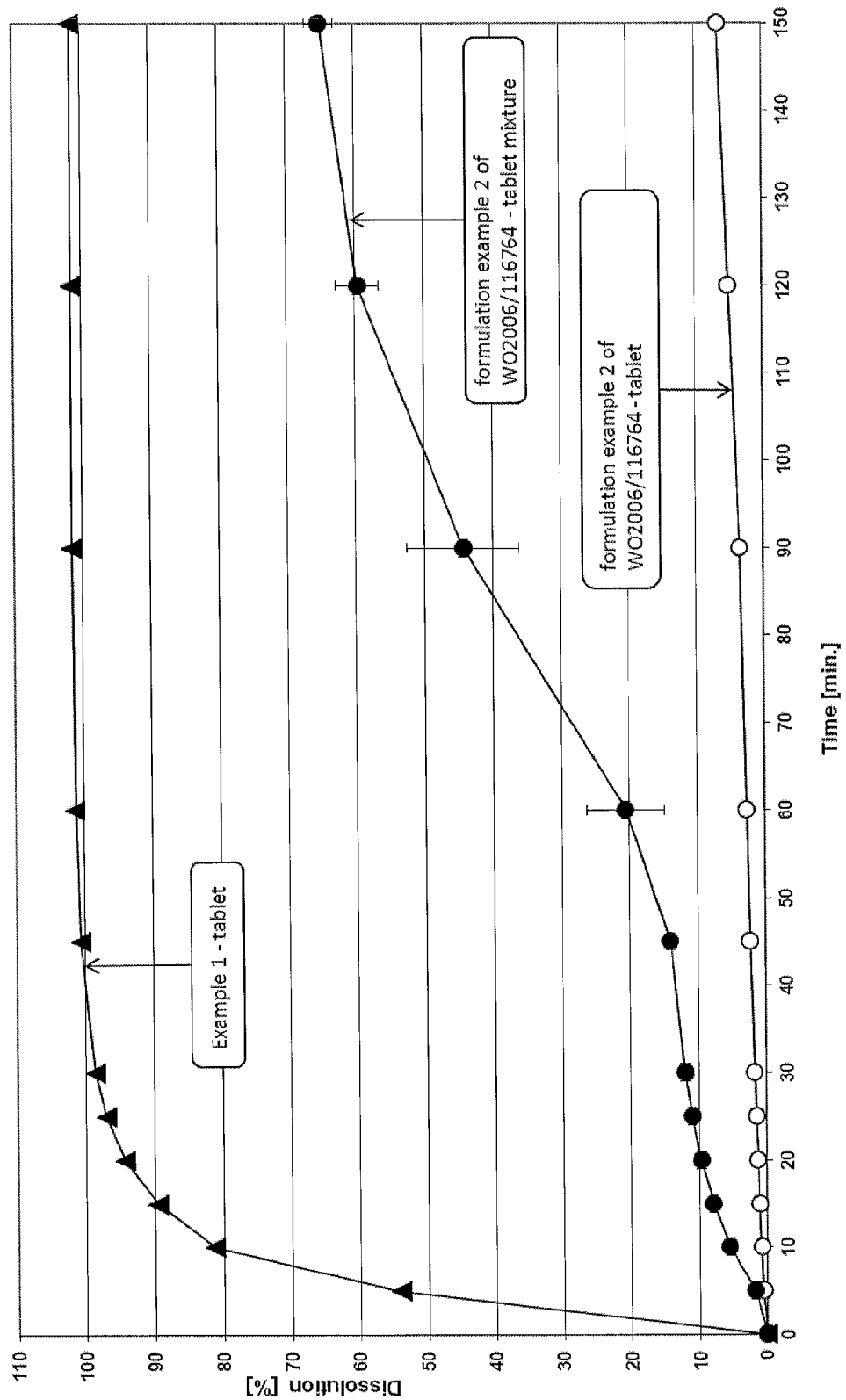
FIG. 1 shows the dissolution profiles of solid pharmaceutical dosage forms according to the invention (Example 1 —tablet) and according to the prior art.
Figure 2:
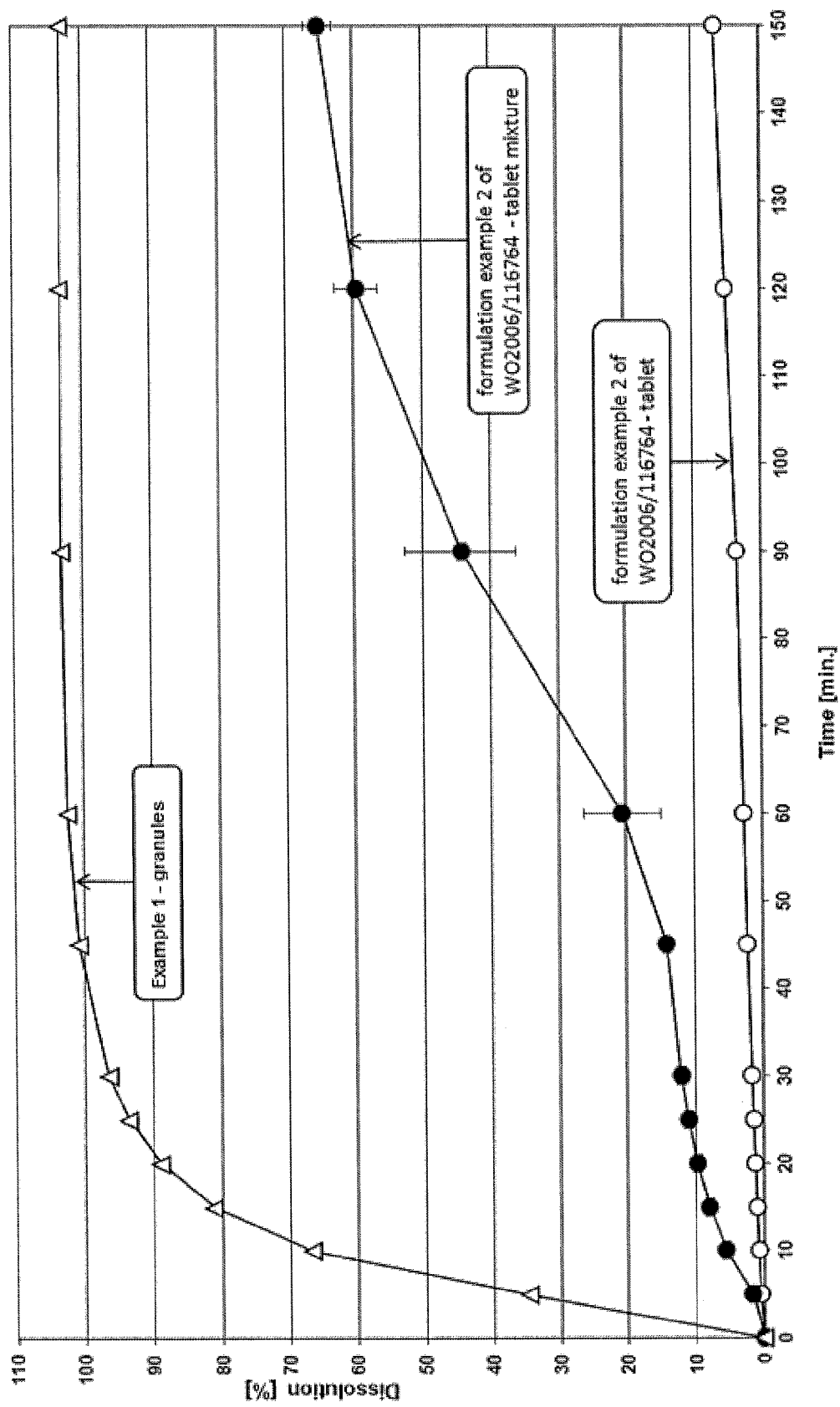
FIG. 2 shows the dissolution profiles of solid pharmaceutical dosage forms according to the invention (Example 1 —granules) and according to the prior art.
Figure 3:
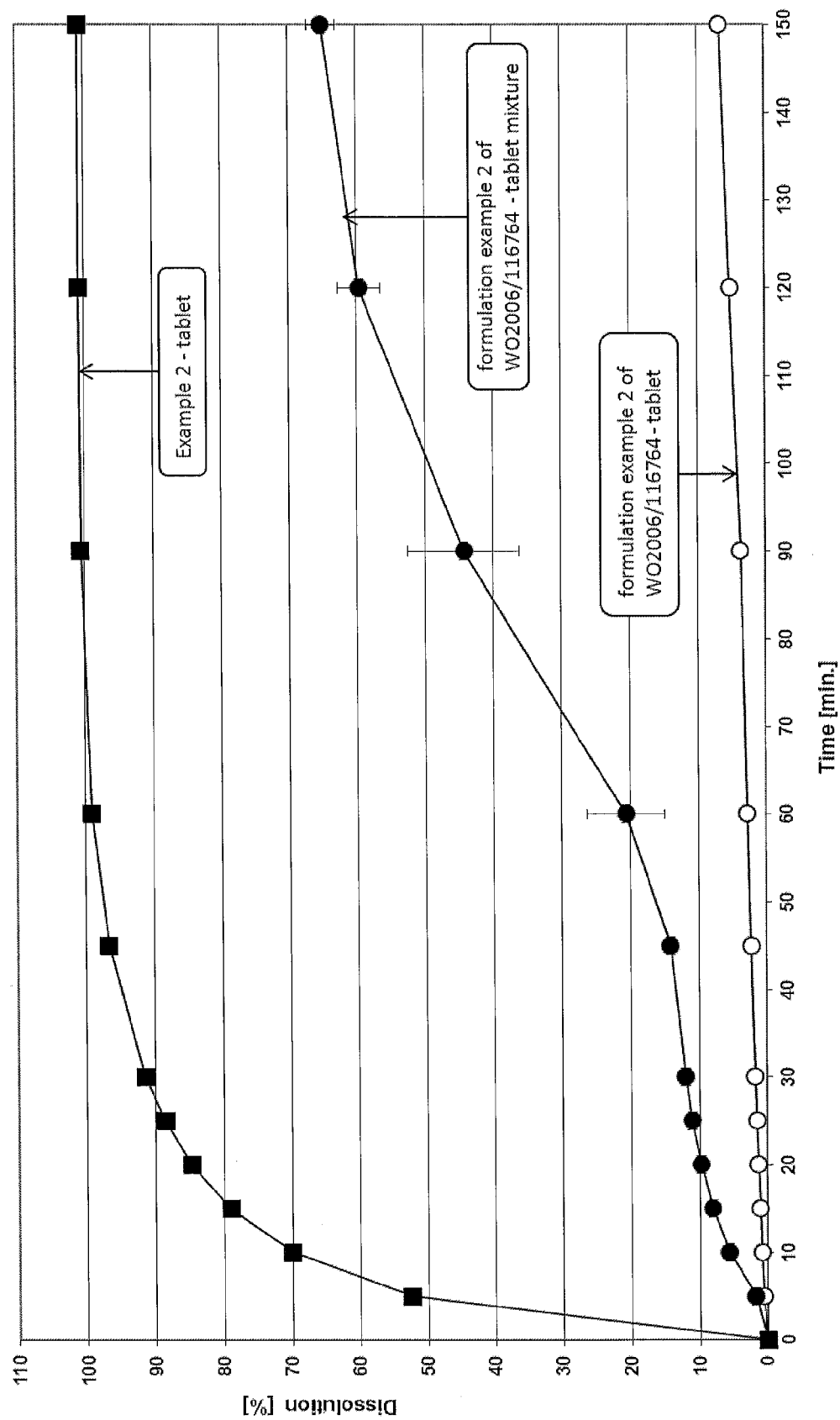
FIG. 3 shows the dissolution profiles of solid pharmaceutical dosage forms according to the invention (Example 2 —tablet) and according to the prior art.
Figure 4:
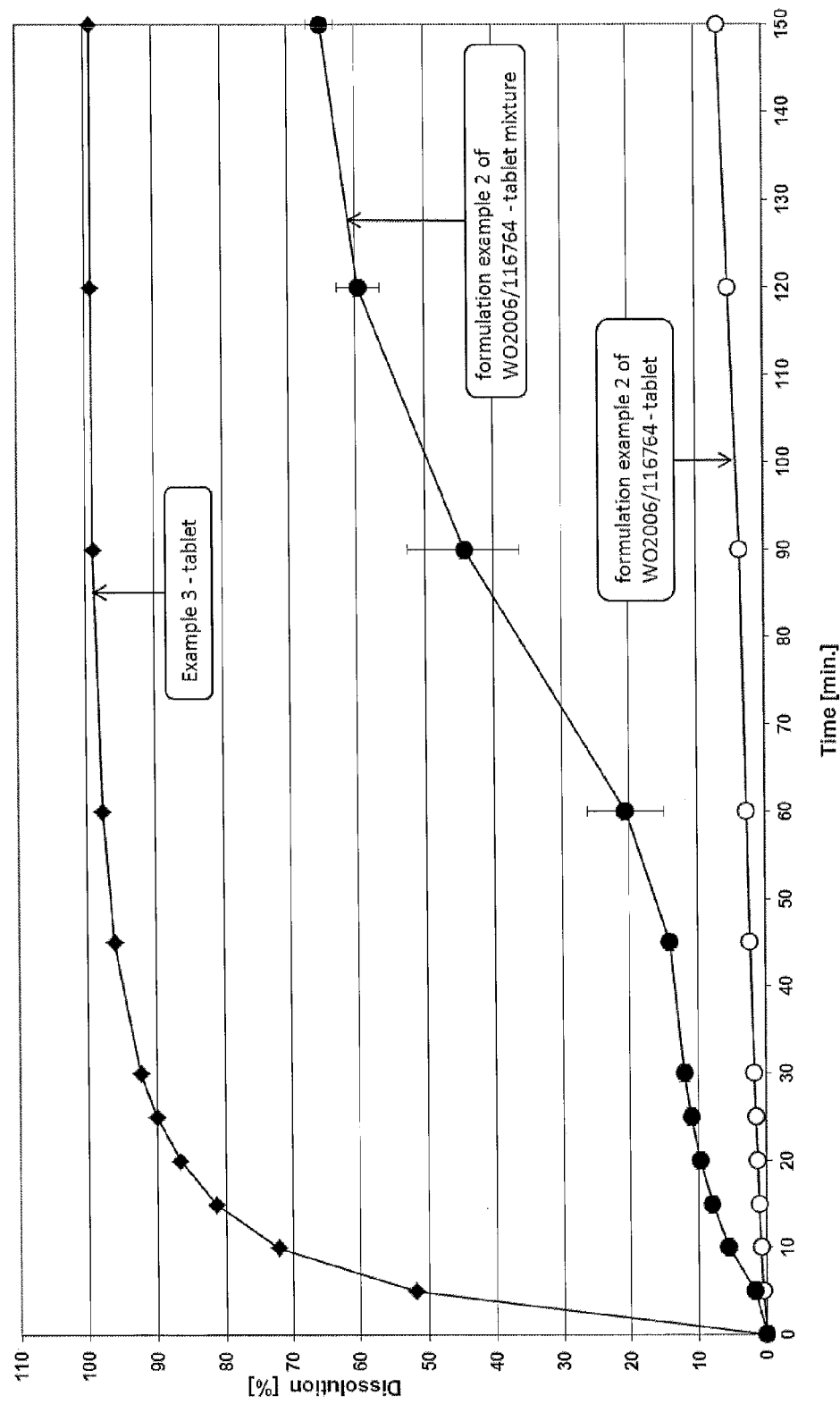
FIG. 4 shows the dissolution profiles of solid pharmaceutical dosage forms according to the invention (Example 3 —tablet) and according to the prior art.

It has surprisingly been found that the addition of a compound comprising an alkaline earth metal ion and/or an alkaline compound results in a superior dissolution rate of the active from the solid pharmaceutical dosage form. Any alkaline earth metal is suitable in the compound comprising an alkaline earth metal ion. Particularly, magnesium and calcium ions are preferred. Therefore, the compound comprising an alkaline earth metal ion can be a magnesium or calcium compound. Also mixed compounds comprising both, magnesium and calcium ions or other ions such as alkali metal ions in addition to the alkaline earth metal ion are suitable. The magnesium or calcium compound may for example be selected from the group consisting of magnesium oxide, magnesium hydroxide, magnesium carbonate, magnesium chloride, magnesium sulfate, magnesium phosphate, calcium oxide, calcium hydroxide, calcium carbonate, calcium chloride, calcium sulfate, calcium phosphate and complexes of $Mg^{2+}$ or $Ca^{2+}$ with organic ligands, such as acetate, citrate or EDTA. Preferably, the compound comprising an alkaline earth metal ion comprises a magnesium ion. A preferred compound comprising an alkaline earth metal ion is magnesium oxide.

Magnesium stearate and calcium stearate are excluded from the compounds comprising an alkaline earth metal ion used in the dosage form of the invention. Preferably, the compound comprising an alkaline earth metal ion is not a salt of stearic acid, more preferably it is not a salt of a fatty acid, more preferably it is not a lubricant. Lubricants, such as magnesium stearate, are known pharmaceutical excipients.

In a further embodiment, the compound comprising an alkaline earth metal ion may be an inorganic compound, such as an oxide, hydroxide, carbonate, halide (in particular chloride), sulfate or phosphate. The compound comprising an alkaline earth metal ion may be hydrophilic.

The solid pharmaceutical dosage form according to the invention may comprise an alkaline compound. In the context of the present invention an "alkaline compound" is defined as a compound which results in a pH above 7 when added to water. The alkaline compound can for example be a hydroxide or carbonate, such as a hydroxide or carbonate of an alkali metal or an alkaline earth metal. The alkaline compound can also be a salt of a weak acid, such as an alkali metal salt or an alkaline earth metal salt of a weak acid.

The weak acid in the salt of a weak acid can be an inorganic acid or an organic acid. The inorganic acid can be for example phosphoric acid. Suitable organic acids are for example lactic acid, acetic acid, citric acid and oxalic acid.

Magnesium stearate and calcium stearate are excluded from the alkaline compounds used in the dosage form of the invention. If the alkaline compound is a salt of a weak acid, the acid preferably is not stearic acid, more preferably the acid is not a fatty acid.

Preferably, the solid pharmaceutical dosage form according to the invention comprises a compound comprising an alkaline earth metal ion, in particular a magnesium ion, most preferably magnesium oxide. In another preferred embodiment, the solid pharmaceutical dosage form comprises an alkaline compound selected from sodium or potassium citrate and sodium or potassium dihydrogenphosphate, hydrogenphosphate or phosphate.

The amount of the compound comprising an alkaline earth metal ion and/or an alkaline compound added to the dosage form is not particularly limited and can be selected by a person skilled in the art according to the requirements for example with respect to the desired dissolution rate or compressibility of prepared tablets. Suitably, dolutegravir or a pharmaceutically acceptable salt or solvate thereof and the compound comprising an alkaline earth metal ion and/or an alkaline compound are present in a molar ratio of from 1:10 to 10:1, preferably of from 1:5 to 5:1, more preferably of from 1:3 to 3:1 and most preferably of from 1:2 to 2:1.

A solid pharmaceutical dosage form may for example contain 0.5 to 15% by weight of the compound comprising an alkaline earth metal ion and/or an alkaline compound based on the total weight of the dosage form, preferably from 1 to 8% by weight, more preferably from 3 to 5% by weight. The total weight of the dosage form is considered as the total weight of for example a tablet without coating or the total weight of a capsule fill without the weight of the capsule shell.

The solid pharmaceutical dosage form may comprise one or more further pharmaceutically acceptable excipients, such as e.g. fillers, binder, disintegrants, glidants, surfactants and flow regulators ("Lexikon der Hilfsstoffe für Pharmazie, Kosmetik and angrenzende Gebiete", edited by H. P. Fiedler, $5^{th}$ Edition, and "Handbook of Pharmaceutical Excipients", $6^{th}$ Edition, edited by Arthur H. Kibbe, American Pharmaceutical Association, Washington, USA, and Pharmaceutical Press, London).

Fillers: The pharmaceutical dosage form can contain one or more filler(s). In general, a filler is a substance that increases the bulk volume of the mixture and thus the size of the resulting pharmaceutical dosage form. Preferred examples of fillers are selected from sugar, microcrystalline cellulose, lactose starch and mixtures thereof. The filler may be present in a proportion of 0 to 80% by weight, preferred between 10 and 60% by weight of the total weight of the dosage form.

Binders: Binders are adhesives to promote size enlargement to produce granules and thus improve flowability of the blend during the manufacturing process. Binders may also improve the hardness of the tablets by enhancing intragranular as well as intergranular forces. Preferred binders for wet granulation are povidone, tragacanth, sodium alginate, gum arabic, starch pregelatinized, gelatin and cellulosic derivates. The dosage form of the invention may, for example, comprise the following hydrophoilic poymers as binder: polysaccharides, such as hydroxypropyl methyl cellulose (HPMC) e.g. Pharmacoat 603®. Typically, the binder is present in an amount of 0 to 40% by weight, preferably between 2 and 10% by weight of the total weight of the pharmaceutical dosage form.

Lubricants: Lubricants are agents which act on the flowability of the powder by reducing interparticle friction and cohesion to be compressed. Suitable lubricants colloidal silicon dioxide, such as aerosol, talc, stearic acid, magnesium stearate, calcium stearate, glyceryl behenate, sodium stearyl fumarate and silica gel. Typically, the lubricants are water insoluble and lipophilic. They may be present in an amount of 0 to 5% by weight, preferably between 0.1 and 3% by weight of the total weight of the pharmaceutical dosage form. The magnesium and calcium ion containing lubricants do not contribute to the compound comprising an alkaline earth metal ion and the alkaline compound.

Surfactant: The term "surfactant" refers to an excipient that lowers the surface tension of a liquid. Examples of surfactant include tween 80, polyoxyethylene-polyoxypropylene copolymer and sodium lauryl sulfate. Typically, the surfactant is present in an amount of 0 to 2% by weight, preferably between 0.4 and 1% by weight of the total weight of the pharmaceutical dosage form.

Disintegrants: The term "disintegrant" refers to an excipient which expands and dissolve when wet causing the tablet to break apart in the digestive tract, releasing the active ingredients for absorption. The dissolution profile of a pharmaceutical composition in powdery or granulated form without disintegrant and the same composition compressed into tablets with disintegrant should be essentially the same. Preferred disintegrants are croscarmellose sodium (e.g. Ac-Di-Sol®), sodium carboxymethyl starch, cross-linked polyvinylpyrrolidone (crospovidon), sodium carboxymethyl glycolate and sodium bicarbonate. Typically, the disintegrant is present in an amount of 0 to 30% by weight, preferably between 3 and 15% by weight of the total weight of the pharmaceutical dosage form.

Flow regulators: As flow regulator there can be used e.g. colloidal silica (e.g. Aerosil®). Preferably the flow regulator is present in an amount of 0 to 5% by weight, more preferably in an amount between 1 and 4% by weight of the total weight of the dosage form.

In a preferred embodiment the solid pharmaceutical dosage form of the present invention comprises at least one disintegrant, such as crosscarmelose sodium, for example in an amount of from 1 to 6% by weight of the total weight of the dosage form.

The solid pharmaceutical dosage form of the invention preferably is an oral dosage form, such as capsules, tablets, pellets or sachets. Tablets are particularly preferred. The tablets may or may not have a coating.

In a further embodiment the solid pharmaceutical dosage form of the present invention is obtainable by wet granulation. In the preparation by wet granulation preferably water is used as granulation liquid. The preparation of the solid pharmaceutical dosage form by wet granulation has the advantage that disadvantages of dolutegravir regarding insufficient flowability and the tendency to sticking as well as disadvantages associated with the very high volume of the active are overcome. The granules obtained by wet granulation can either be used for the preparation of capsules, they can be filled into sachets or they can be compressed into tablets.

In the solid pharmaceutical dosage form according to the invention the dissolution rate of the active is significantly increased. The dissolution rate can be measured using USP paddle Apparatus II in 900 ml 0.1 N HCl, pH 1.2, at 37° C. and 100 rpm, increasing the rotation speed to 150 rpm after 90 minutes.

The present invention therefore also relates to a solid pharmaceutical dosage form comprising dolutegravir or a pharmaceutically acceptable salt or solvate thereof, from which at least 10% of the total amount of the dolutegravir present in the dosage form are dissolved in less than 10 minutes when measured using the above described method. Preferably, at least 70% of the total amount of dolutegravir present in the dosage form are dissolved in less than 20 minutes. These solid pharmaceutical dosage forms may comprise a compound comprising an alkaline earth metal ion and/or an alkaline compound, in particular magnesium oxide and/or may be obtainable by wet granulation and furthermore can make use of all of the preferred embodiments described above.

The dolutegravir can be present in the solid pharmaceutical dosage form of the present invention either in its free form or in the form of a pharmaceutically acceptable salt or solvate thereof. Pharmaceutically acceptable salts or solvates are known to a person skilled in the art and can be prepared for example by the addition of known acids or bases. Preferably, the dolutegravir is present as dolutegravir sodium salt. As solvate the hydrate is preferred.

Advantageously, the dolutegravir sodium salt is crystalline.

Figure 19:
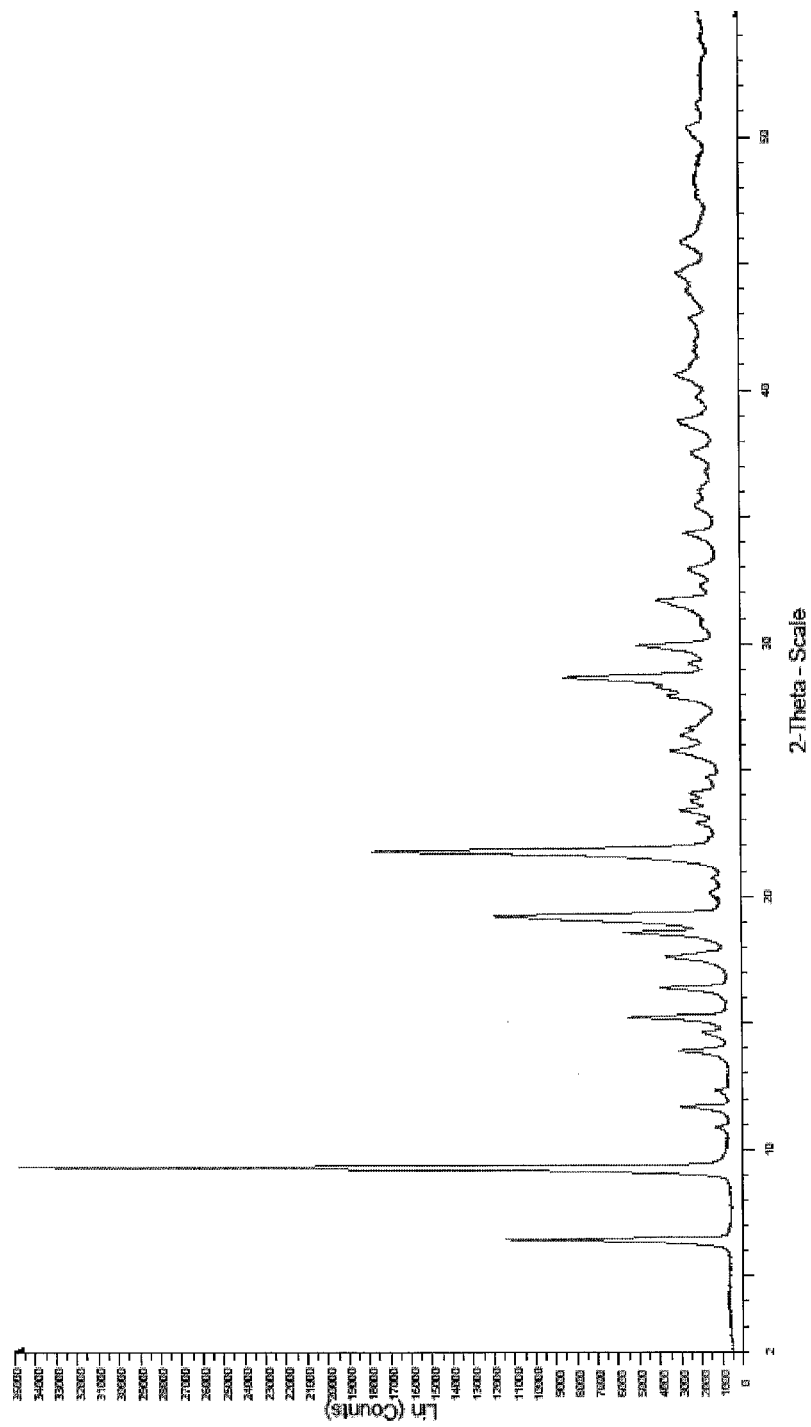
FIG. 19 shows the X-ray powder diffraction pattern of dolutegravir sodium salt.

In one embodiment, the solid pharmaceutical dosage form of the present invention contains a crystalline form of dolutegravir sodium salt which has diffraction peaks in an X-ray powder diffraction pattern at 6.4±0.2 and 9.2±0.2 degrees 2-theta, preferably at 6.4±0.2, 9.2±0.2 and 13.8±0.2 degrees 2-theta, more preferably at 6.4±0.2, 9.2±0.2, 13.8±0.2 and 19.2±0.2 degrees 2-theta, even more preferably at 6.4±0.2, 9.2±0.2, 13.8±0.2, 19.2±0.2 and 21.8±0.2 degrees 2-theta and most preferably at 6.4±0.2, 9.2±0.2, 13.8±0.2, 14.6±0.2, 15.2±0.2, 17.6±0.2, 19.2±0.2, 21.8±0.2, 24.1±0.2 and 28.7±0.2 degrees 2-theta. The crystalline form of the dolutegravir sodium salt in a particularly preferred embodiment has an X-ray powder diffraction pattern substantially as shown in FIG. 19 when measured using Cu k alpha radiation.

The preparation of crystalline dolutegravir sodium salt and the above described polymorph of this salt is disclosed in WO2010/068253.

The present invention furthermore relates to a method of preparation of a solid pharmaceutical dosage form as described above, the method comprising the steps of mixing dolutegravir or a pharmaceutically acceptable salt or solvate thereof with a compound comprising an alkaline earth metal ion and/or an alkaline compound and optionally further ingredients, and wet granulation of the obtained mixture. The method may further comprise the step of compressing the obtained granules.

Finally, the present invention also relates to the above described solid pharmaceutical dosage form for use in a method of treatment of a HIV infection in a human.

The invention will now be further explained by way of examples which are not intended as limiting.

EXAMPLES

Example 1

Tablets were prepared using the ingredients as summarized in the following table 1.

TABLE 1

| Compound | Brand ® | amount [mg] | amount [%] |
|---|---|---|---|
| intragranular | | | |
| Dolutegravir sodium | — | 50.00* | 21.11 |
| HPMC | Pharmacoat 603 | 8.00 | 3.38 |
| Lactose monohydrate | FlowLac 100 (spray dried) | 60.00 | 25.33 |
| Croscarmellose sodium | Ac-Di-Sol | 5.00 | 2.11 |
| Microcrystalline cellulose | Avicel PH 101 | 50.00 | 21.11 |
| Sodium lauryl sulphate (SDS) | — | 2.00 | 0.84 |
| Magnesium oxide | — | 8.00 | 3.38 |
| extragranular | | | |
| Magnesium stearate | — | 2.90 | 1.22 |
| Croscarmellose sodium | Ac-Di-Sol | 5.00 | 2.11 |
| Microcrystalline cellulose + Colloidal silica | Prosolv SMCC 90 | 46.00 | 19.42 |
| TOTAL | | 236.90 | 100.00 |

*based on the free acid of dolutegravir

Manufacturing Description

An aqueous solution comprising Pharmacoat 603 and Magnesium oxide was prepared. Agitation was required in order to achieve complete suspension. Dolutegravir sodium, SDS, FlowLac 100, Prosolv SMCC 90 and half the amount of Ac-Di-Sol were granulated with the before prepared solution. The obtained granules were sieved through 2000 μm mesh size and subsequently dried at 40° C. After sieving the dried granules through 630 μm mesh size remaining quantity of Ac-Di-Sol and Prosolv SMCC 90 were added. The mixture was blended for 10 minutes in a Turbula T10B tumble mixer. After addition of Magnesium stearate blending was continued for further 3 minutes. Finally, the blend was compressed into tablets on an eccentric press (e.g. Korsch Ek0) with a 9 mm biconvex tablet punch.

Example 2

Tablets were prepared using the ingredients as summarized in the following table 2.

TABLE 2

| Compound | Brand ® | amount [mg] | amount [%] |
|---|---|---|---|
| intragranular | | | |
| Dolutegravir sodium | — | 50.00* | 21.11 |
| HPMC | Pharmacoat 603 | 8.00 | 3.38 |
| Microcrystalline cellulose + Colloidal silica | Prosolv SMCC 90 | 120.00 | 50.65 |
| Croscarmellose sodium | Ac-Di-Sol | 5.00 | 2.11 |
| Sodium lauryl sulphate (SDS) | — | 2.00 | 0.84 |
| Magnesium oxide | — | 8.00 | 3.38 |
| extragranular | | | |
| Magnesium stearate | — | 2.90 | 1.22 |
| Croscarmellose sodium | Ac-Di-Sol | 5.00 | 2.11 |
| Microcrystalline cellulose + Colloidal silica | Prosolv SMCC 90 | 36.00 | 15.20 |
| TOTAL | | 236.90 | 100.00 |

*based on the free acid of dolutegravir

Manufacturing Description

An aqueous solution comprising Pharmacoat 603 and Magnesium oxide was prepared. Agitation was required in order to achieve complete suspension. Dolutegravir sodium, SDS, Prosolv SMCC 90 and half the amount of Ac-Di-Sol were granulated with the before prepared solution. The obtained granules were sieved through 2000 μm mesh size and subsequently dried at 40° C. After sieving the dried granules through 630 μm mesh size remaining quantity of Ac-Di-Sol and Prosolv SMCC 90 were added. The mixture was blended for 10 minutes in a Turbula T10B tumble mixer. After addition of Magnesium stearate blending was continued for further 3 minutes. Finally, the blend was compressed into tablets on an eccentric press (e.g. Korsch Ek0) with a 9 mm biconvex tablet punch.

Example 3

Tablets were prepared using the ingredients as summarized in the following table 3.

TABLE 3

| Compound | Brand ® | amount [mg] | amount [%] |
|---|---|---|---|
| intragranular | | | |
| Dolutegravir sodium | — | 50.00* | 21.11 |
| HPMC | Pharmacoat 603 | 8.00 | 3.38 |
| Lactose monohydrate | Granulac 200 (milled Lactose) | 60.00 | 25.33 |
| Microcrystalline cellulose | Avicel PH 101 | 50.00 | 21.11 |
| Croscarmellose sodium | Ac-Di-Sol | 5.00 | 2.11 |
| Sodium lauryl sulphate (SDS) | — | 2.00 | 0.84 |
| Magnesium oxide | — | 8.00 | 3.38 |
| extragranular | | | |
| Magnesium stearate | — | 2.90 | 1.22 |
| Croscarmellose sodium | Ac-Di-Sol | 5.00 | 2.11 |
| Microcrystalline cellulose + Colloidal silica | Prosolv SMCC 90 | 46.00 | 15.20 |
| TOTAL | | 236.90 | 100.00 |

*based on the free acid of dolutegravir

Manufacturing Description

An aqueous solution comprising Pharmacoat 603 and Magnesium oxide was prepared. Agitation was required in order to achieve complete suspension. Dolutegravir sodium, SDS, Granulac 200 and half the amount of Ac-Di-Sol were granulated with the before prepared solution. The obtained granules were sieved through 2000 μm mesh size and subsequently dried at 40° C. After sieving the dried granules through 630 μm mesh size remaining quantity of Ac-Di-Sol and Prosolv SMCC 90 were added. The mixture was blended for 10 minutes in a Turbula T10B tumble mixer. After addition of Magnesium stearate blending was continued for further 3 minutes. Finally, the blend was compressed into tablets on an eccentric press (e.g. Korsch Ek0) with a 9 mm biconvex tablet punch.

Example 4

Tablets were prepared using the ingredients as summarized in the following table.

TABLE 4

| Compound | Brand ® | amount [mg] | amount [%] |
|---|---|---|---|
| intragranular | | | |
| Dolutegravir sodium | — | 53.24* | 22.17 |
| HPMC | Pharmacoat 603 | 8.00 | 3.33 |

TABLE 4-continued

| Compound | Brand ® | amount [mg] | amount [%] |
|---|---|---|---|
| Lactose monohydrate | FlowLac 100 (spray dried) | 60.00 | 24.99 |
| Croscarmellose sodium | Ac-Di-Sol | 5.00 | 2.08 |
| Microcrystalline cellulose | Avicel PH 101 | 50.00 | 20.82 |
| Sodium lauryl sulphate (SDS) | — | 2.00 | 0.83 |
| Magnesium oxide | — | 8.00 | 3.33 |
| extragranular | | | |
| Magnesium stearate | — | 2.90 | 1.21 |
| Croscarmellose sodium | Ac-Di-Sol | 5.00 | 2.08 |
| Microcrystalline cellulose + Colloidal silica | Prosolv SMCC 90 | 46.00 | 19.16 |
| TOTAL | | 240.14 | 100.00 |

*adapted to free acid of dolutegravir

Manufacturing Description

An aqueous solution comprising Pharmacoat 603 and Magnesium oxide was prepared. Agitation was required in order to achieve complete suspension. Dolutegravir sodium, SDS, FlowLac 100, Prosolv SMCC 90 and half the amount of Ac-Di-Sol were granulated with the before prepared solution. The obtained granules were sieved through 2000 μm mesh size and subsequently dried at 40° C. After sieving the dried granules through 630 μm mesh size remaining quantity of Ac-Di-Sol and Prosolv SMCC 90 were added. The mixture was blended for 10 minutes in a Turbula T10B tumble mixer. After addition of Magnesium stearate blending was continued for further 3 minutes. Finally, the blend was compressed into tablets on an eccentric press (e.g. Korsch Ek0) with a 9 mm biconvex tablet punch.

Example 5

Tablets were prepared using the ingredients as summarized in the following table.

TABLE 5

| Compound | Brand ® | amount [mg] | amount [%] |
|---|---|---|---|
| intragranular | | | |
| Dolutegravir sodium | — | 53.24* | 22.17 |
| HPMC | Pharmacoat 603 | 8.00 | 3.33 |
| Lactose monohydrate | FlowLac 100 (spray dried) | 61.00 | 25.42 |
| Croscarmellose sodium | Ac-Di-Sol | 5.00 | 2.08 |
| Microcrystalline cellulose | Avicel PH 101 | 50.86 | 21.19 |
| Sodium lauryl sulphate (SDS) | — | — | — |
| Magnesium oxide | — | 8.00 | 3.33 |
| extragranular | | | |
| Magnesium stearate | — | 2.90 | 1.21 |
| Croscarmellose sodium | Ac-Di-Sol | 5.00 | 2.08 |
| Microcrystalline cellulose + Colloidal silica | Prosolv SMCC 90 | 46.00 | 19.17 |
| TOTAL | | 240.00 | 100.00 |

*adapted to free acid of dolutegravir

Manufacturing Description

An aqueous solution comprising Pharmacoat 603 and Magnesium oxide was prepared. Agitation was required in order to achieve complete suspension. Dolutegravir sodium, FlowLac 100, Prosolv SMCC 90 and half the amount of Ac-Di-Sol were granulated with the before prepared solution. The obtained granules were sieved through 2000 μm mesh size and subsequently dried at 40° C. After sieving the dried granules through 630 μm mesh size remaining quantity of Ac-Di-Sol and Prosolv SMCC 90 were added. The mixture was blended for 10 minutes in a Turbula T10B tumble mixer. After addition of Magnesium stearate blending was continued for further 3 minutes. Finally, the blend was compressed into tablets on an eccentric press (e.g. Korsch Ek0) with a 9 mm biconvex tablet punch.

Example 6

Tablets were prepared using the ingredients as summarized in the following table.

TABLE 6

| Compound | Brand ® | amount [mg] | amount [%] |
|---|---|---|---|
| intragranular | | | |
| Dolutegravir sodium | — | 50.00* | 22.18 |
| HPMC | Pharmacoat 603 | 8.00 | 3.33 |
| Lactose monohydrate | FlowLac 100 (spray dried) | 60.00 | 25.00 |
| Croscarmellose sodium | Ac-Di-Sol | 5.00 | 2.08 |
| Microcrystalline cellulose | Avicel PH 101 | 44.86 | 18.69 |
| Sodium lauryl sulphate (SDS) | — | 2.00 | 0.83 |
| Calcium carbonate | — | 13.00 | 5.42 |
| extragranular | | | |
| Magnesium stearate | — | 2.90 | 1.21 |
| Croscarmellose sodium | Ac-Di-Sol | 5.00 | 2.08 |
| Microcrystalline cellulose + Colloidal silica | Prosolv SMCC 90 | 46.00 | 19.17 |
| TOTAL | | 240.00 | 100.00 |

Manufacturing Description

An aqueous solution comprising Pharmacoat 603 and Calcium carbonate was prepared. Agitation was required in order to achieve complete suspension. Dolutegravir sodium, SDS, FlowLac 100, Prosolv SMCC 90 and half the amount of Ac-Di-Sol were granulated with the before prepared solution. The obtained granules were sieved through 2000 μm mesh size and subsequently dried at 40° C. After sieving the dried granules through 630 μm mesh size remaining quantity of Ac-Di-Sol and Prosolv SMCC 90 were added. The mixture was blended for 10 minutes in a Turbula T10B tumble mixer. After addition of Magnesium stearate blending was continued for further 3 minutes. Finally, the blend was compressed into tablets on an eccentric press (e.g. Korsch Ek0) with a 9 mm biconvex tablet punch.

Example 7

Tablets were prepared using the ingredients as summarized in the following table.

TABLE 7

| Composition | Brand ® | Functionality | Amount [mg] | [%] |
|---|---|---|---|---|
| intragranular | | | | |
| Dolutegravir sodium | — | active ingredient | 53.24* | 22.18 |

TABLE 7-continued

| Composition | Brand ® | Functionality | Amount [mg] | Amount [%] |
|---|---|---|---|---|
| HPMC | Pharmacoat 603 | binder | 8.00 | 3.33 |
| Sodium lauryl sulphate | — | surfactant | 5.00 | 2.08 |
| Lactose monohydrate | FlowLac 100 | filler | 50.63 | 21.10 |
| Microcrystalline cellulose | Avicel PH 101 | filler | 50.63 | 21.10 |
| Croscarmellose sodium | Ac-Di-Sol | disintegrant | 5.00 | 2.08 |
| 1. Sodium carbonate | — | basic compound | 12.60 | 5.25 |
| extragranular | | | | |
| Croscarmellose sodium | Ac-Di-Sol | disintegrant | 5.00 | 2.08 |
| Microcrystalline cellulose + Silica, colloidal anhydrous | Prosolv SMCC 90 | filler/glidant | 50.00 | 20.83 |
| Magnesium stearat | — | lubricant | 2.90 | 1.21 |
| Total | | | 240.00 | 100.0 |

*adapted to the potency of the active

Manufacturing Description

An aqueous solution comprising Pharmacoat 603 and Sodium carbonate was prepared. Agitation was required in order to achieve a homogenous solution. The active, Flow-Lac 100, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Ac-Di-Sol and Prosolv SMCC 90 were added. The mixture was blended for 10 minutes in a Turbula T10B tumble mixer. After addition of Magnesium stearate blending was continued for 3 minutes. Finally, the blend was compressed into tablets on an eccentric press Ek0 with a 9 mm biconvex tablet punch.

Comparative Example 1 (According to Example 1 of WO2006/116764)

TABLE 8

| Compound | Brand ® | amount [mg] | amount [%] |
|---|---|---|---|
| Dolutegravir sodium | — | 53.24* | 55.46 |
| Starch (dried) | Starcap 1500 (dried) | 40.76 | 42.46 |
| Magnesium stearate | — | 2.00 | 2.08 |
| TOTAL | | 96.00 | 100.00 |

*based on the free acid of dolutegravir

Manufacturing Description

Ingredients are mixed and filled into a hard gelatine capsule.

Comparative Example 2 (According to Example 1 of WO2006/116764)

TABLE 9

| Compound | Brand ® | amount [mg] | amount [%] |
|---|---|---|---|
| Dolutegravir sodium | — | 53.24* | 54.33 |
| Starch (dried) | Starcap 1500 (dried) | 40.76 | 41.59 |

TABLE 9-continued

| Compound | Brand ® | amount [mg] | amount [%] |
|---|---|---|---|
| Magnesium stearate | — | 4.00 | 4.08 |
| TOTAL | | 98.00 | 100.00 |

*based on the free acid of dolutegravir

Manufacturing Description

Ingredients are mixed and filled into a hard gelatine capsule.

Comparative Example 3 (According to Example 1 of WO2006/116764)

TABLE 10

| Compound | Brand ® | amount [mg] | amount [%] |
|---|---|---|---|
| Dolutegravir sodium | — | 53.24* | 53.24 |
| Starch (dried) | Starcap 1500 (dried) | 40.76 | 40.76 |
| Magnesium stearate | — | 6.00 | 6.00 |
| TOTAL | | 100.00 | 100.00 |

*based on the free acid of dolutegravir

Manufacturing Description

Ingredients are mixed and filled into a hard gelatine capsule.

Comparative Example 4 (According to Example 2 of WO 2006/116764)

Tablet Mixture

TABLE 11

| Compound | Brand ® | amount [mg] | amount [%] |
|---|---|---|---|
| Dolutegravir sodium | — | 50.00* | 37.5 |
| Microcrystalline cellulose | Avicel PH 101 | 80.00 | 60.2 |
| Silicon dioxide | Aerosil | 2.00 | 1.5 |
| Stearic acid | — | 1.00 | 0.8 |
| TOTAL | | 133.00 | 100.00 |

*based on the free acid of dolutegravir

All ingredients are mixed together in order to get tablet mixture.

The tablet mixture was compressed in order to get tablets.

Comparative Example 5

Tablets were prepared using the ingredients as summarized in the following table.

TABLE 12

| Composition | Brand ® | Functionality | Amount [mg] | [%] |
|---|---|---|---|---|
| intragranular | | | | |
| Dolutegravir sodium | — | active ingredient | 53.10* | 35.40 |
| HPMC | Pharmacoat 603 | binder | 7.00 | 4.67 |
| Sodium lauryl sulphate | — | surfactant | 2.00 | 1.33 |
| Lactose monohydrate | Granulac 200 | filler | 53.00 | 35.33 |
| Microcrystalline cellulose | Avicel PH 101 | filler | 23.90 | 15.93 |
| Croscarmellose sodium | Ac-Di-Sol | disintegrant | 5.00 | 3.33 |
| extragranular | | | | |
| Croscarmellose sodium | Ac-Di-Sol | disintegrant | 5.00 | 3.33 |
| Magnesium stearat | — | lubricant | 1.00 | 0.67 |
| | | Total | 150.00 | 100.0 |

*adapted to the potency of the active

Manufacturing Description

An aqueous solution comprising Pharmacoat 603 was prepared. The active, Granulac 200, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Ac-Di-Sol was added. The mixture was blended for 10 minutes in a Turbula T10B tumble mixer. After addition of Magnesium stearate blending was continued for 3 minutes. Finally, the blend was compressed into tablets on an eccentric press Ek0 with a 7 mm biconvex tablet punch.

Example 8

Tablets were prepared using the ingredients as summarized in the following table.

TABLE 13

| Composition | Brand ® | Functionality | Amount [mg] | [%] |
|---|---|---|---|---|
| intragranular | | | | |
| Dolutegravir sodium | — | active ingredient | 53.10* | 35.40 |
| HPMC | Pharmacoat 603 | binder | 7.00 | 4.67 |
| Sodium lauryl sulphate | — | surfactant | 2.00 | 1.33 |
| Lactose monohydrate | Granulac 200 | filler | 49.00 | 32.67 |
| Microcrystalline cellulose | Avicel PH 101 | filler | 19.90 | 13.27 |
| Croscarmellose sodium | Ac-Di-Sol | disintegrant | 5.00 | 3.33 |
| Magnesium oxide, heavy | — | basic compound | 8.00 | 5.33 |
| extragranular | | | | |
| Croscarmellose sodium | Ac-Di-Sol | disintegrant | 5.00 | 3.33 |
| Magnesium stearat | — | lubricant | 1.00 | 0.67 |
| | | Total | 150.00 | 100.0 |

*adapted to the potency of the active

Manufacturing Description

An aqueous solution comprising Pharmacoat 603 was prepared. The active, Granulac 200, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Ac-Di-Sol was added. The mixture was blended for 10 minutes in a Turbula T10B tumble mixer. After addition of Magnesium stearate blending was continued for 3 minutes. Finally, the blend was compressed into tablets on an eccentric press Ek0 with a 7 mm biconvex tablet punch.

Example 9

Tablets were prepared using the ingredients as summarized in the following table.

TABLE 14

| Composition | Brand ® | Functionality | Amount [mg] | [%] |
|---|---|---|---|---|
| intragranular | | | | |
| Dolutegravir sodium | — | active ingredient | 53.24* | 22.18 |
| HPMC | Pharmacoat 603 | binder | 8.00 | 3.33 |
| Sodium lauryl sulphate | — | surfactant | 2.00 | 0.83 |
| Lactose monohydrate | FlowLac 100 | filler | 55.00 | 22.92 |
| Microcrystalline cellulose | Avicel PH 101 | filler | 55.00 | 22.92 |
| Croscarmellose sodium | Ac-Di-Sol | disintegrant | 5.00 | 2.08 |
| Magnesium oxide, heavy | — | basic compound | 2.41 | 1.00 |
| extragranular | | | | |
| Croscarmellose sodium | Ac-Di-Sol | disintegrant | 5.00 | 2.08 |
| Microcrystalline cellulose + Silica, colloidal anhydrous | Prosolv SMCC 90 | filler/glidant | 51.45 | 21.44 |
| Magnesium stearat | — | lubricant | 2.90 | 1.21 |
| | | Total | 240.00 | 100.0 |

*adapted to the potency of the active

Manufacturing Description

An aqueous solution comprising Pharmacoat 603 and Magnesium oxide was prepared. Agitation was required in order to achieve a homogenous suspension. The active, FlowLac 100, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Ac-Di-Sol and Prosolv SMCC 90 were added. The mixture was blended for 10 minutes in a Turbula T10B tumble mixer. After addition of Magnesium stearate blending was continued for 3 minutes. Finally, the blend was compressed into tablets on an eccentric press Ek0 with a 9 mm biconvex tablet punch.

Example 10

The dissolution profiles of the tablets obtained in examples 1, 2 and 3 as well as the dissolution profile of the granules used in example 1 were measured according to the above described method. For comparison, also the dissolution profile of the tablet obtained in the above comparative example 4 according to example 2 of WO2006/116764 and the dissolution profile of the mixture used in the above preparation of the tablet according to example 2 of WO2006/116764 were also measured according to the above method. However, in order to avoid a possible influence of the salt of dolutegravir on the dissolution rate dolutegravir sodium salt was used in both, the examples according to the invention and the comparative example.

The results of the dissolution tests are summarized in attached FIGS. 1 to 4. It can be seen that the dissolution rate of the active is significantly increased in the mixture and tablets of the present invention compared to the prior art tablet and the mixture used in the preparation of the prior art tablet.

Furthermore, the prior art formulations have been prepared twice. Both batches were analyzed by the dissolution testing. It can be seen that both formulation batches showed significant differences between the dissolution rates. Thus, the prior art formulations do not provide repeatable and reliable dissolution.

Example 11

Figure 5:
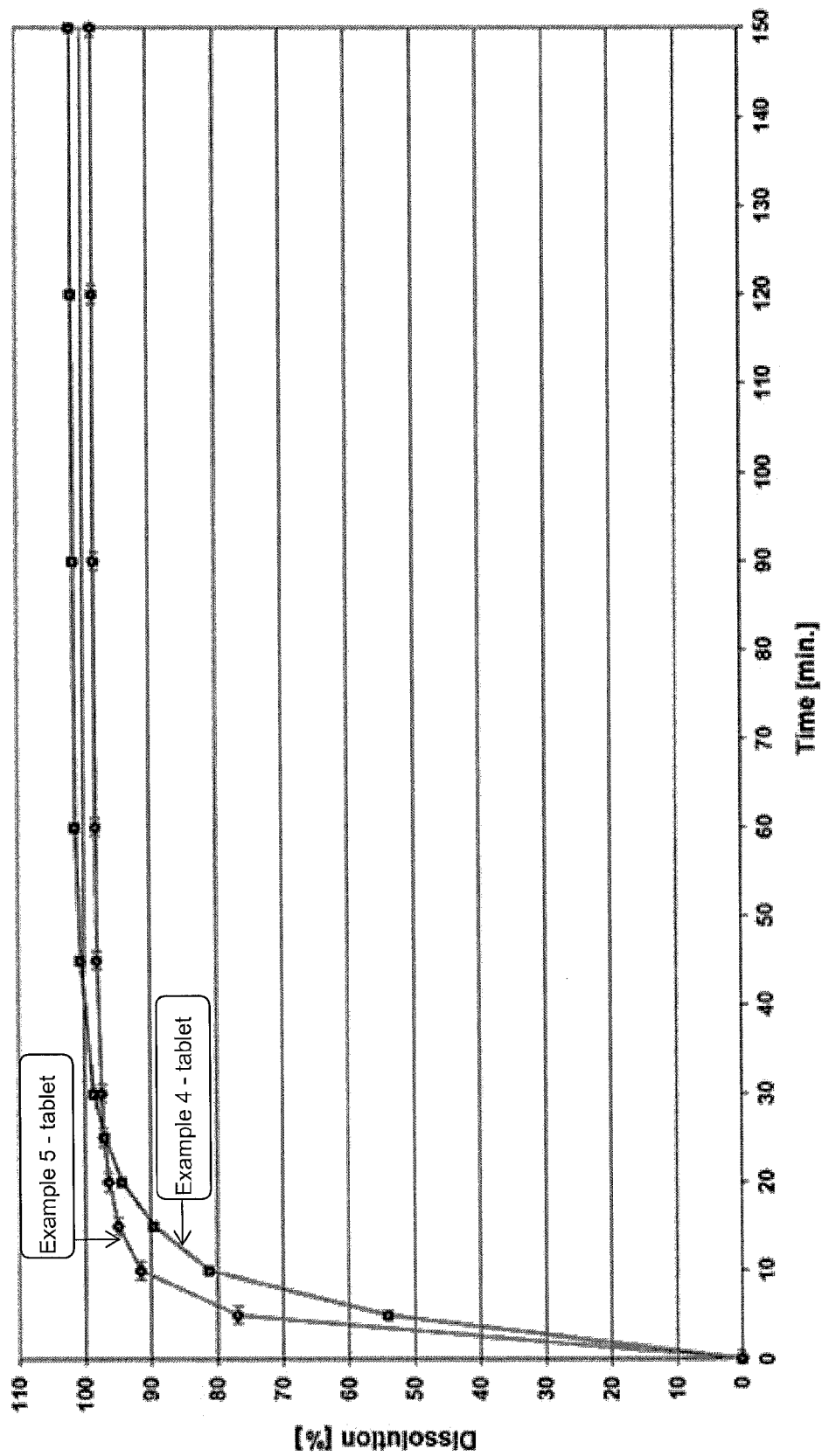
FIG. 5 shows the dissolution profiles of the tablets according to the invention as obtained in examples 4 and 5.
Figure 6:
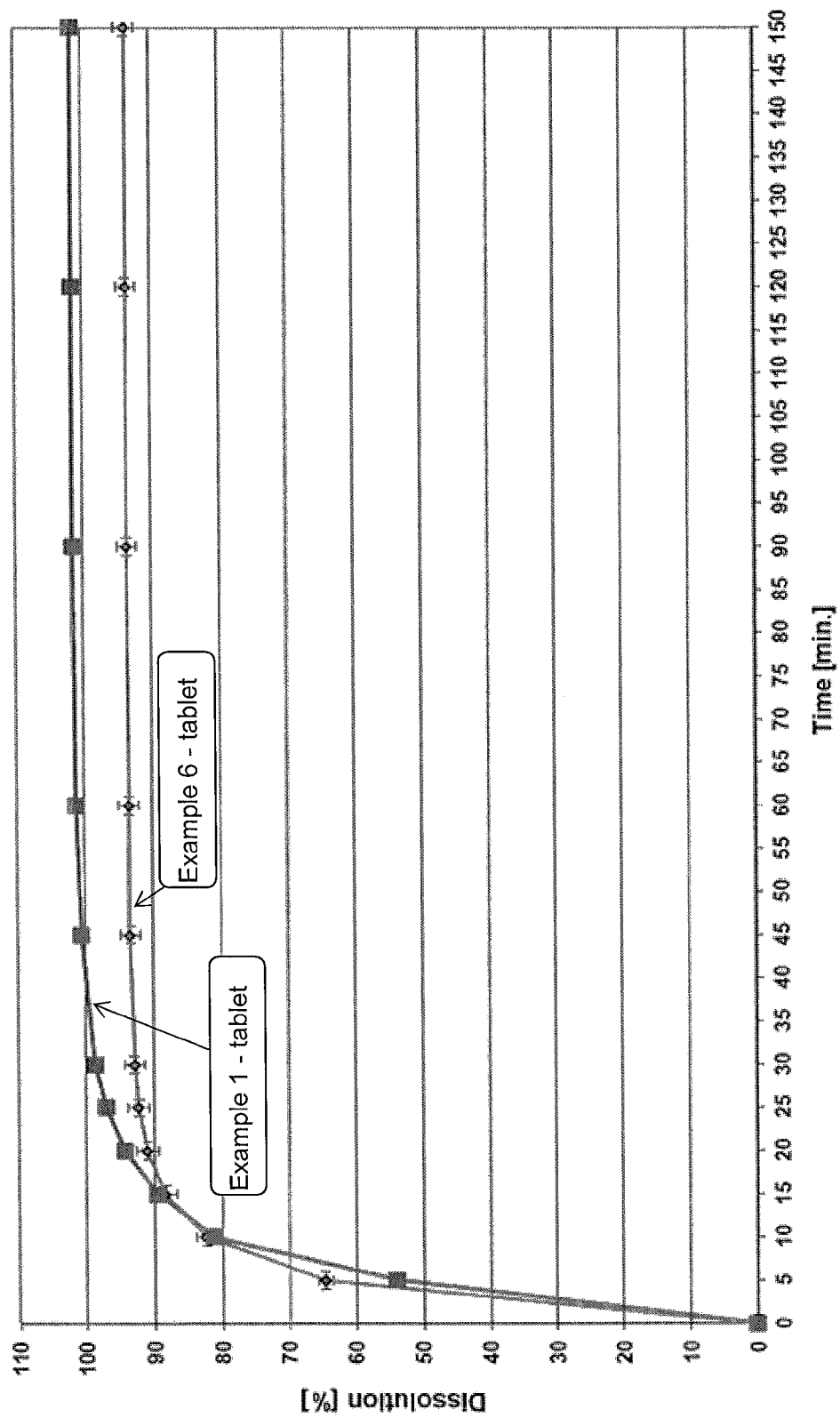
FIG. 6 shows the dissolution profiles of tablets according to the invention as obtained in examples 1 and 6.
Figure 7:
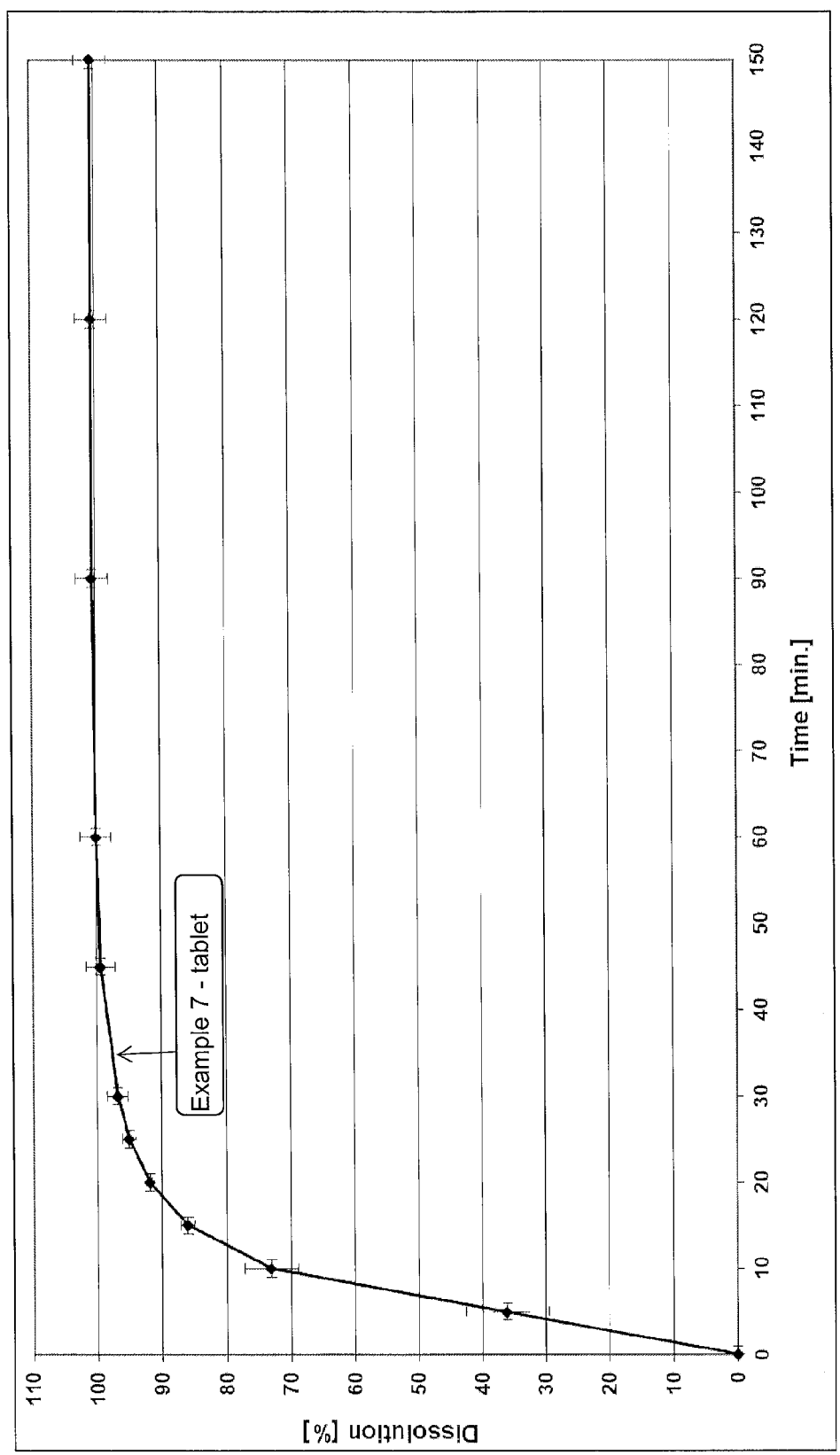
FIG. 7 shows the dissolution profile of tablets according to the invention as obtained in example 7.

The dissolution profiles of the tablets obtained in examples 4, 5, 6 and 7 were measured according to the above described method. The results are summarized in attached FIGS. 5, 6 and 7. It can be seen that the dissolution rate of the active is excellent and that this beneficial effect is obtained by different additives, such as magnesium oxide, calcium carbonate and sodium carbonate, respectively.

Example 12

Figure 8:
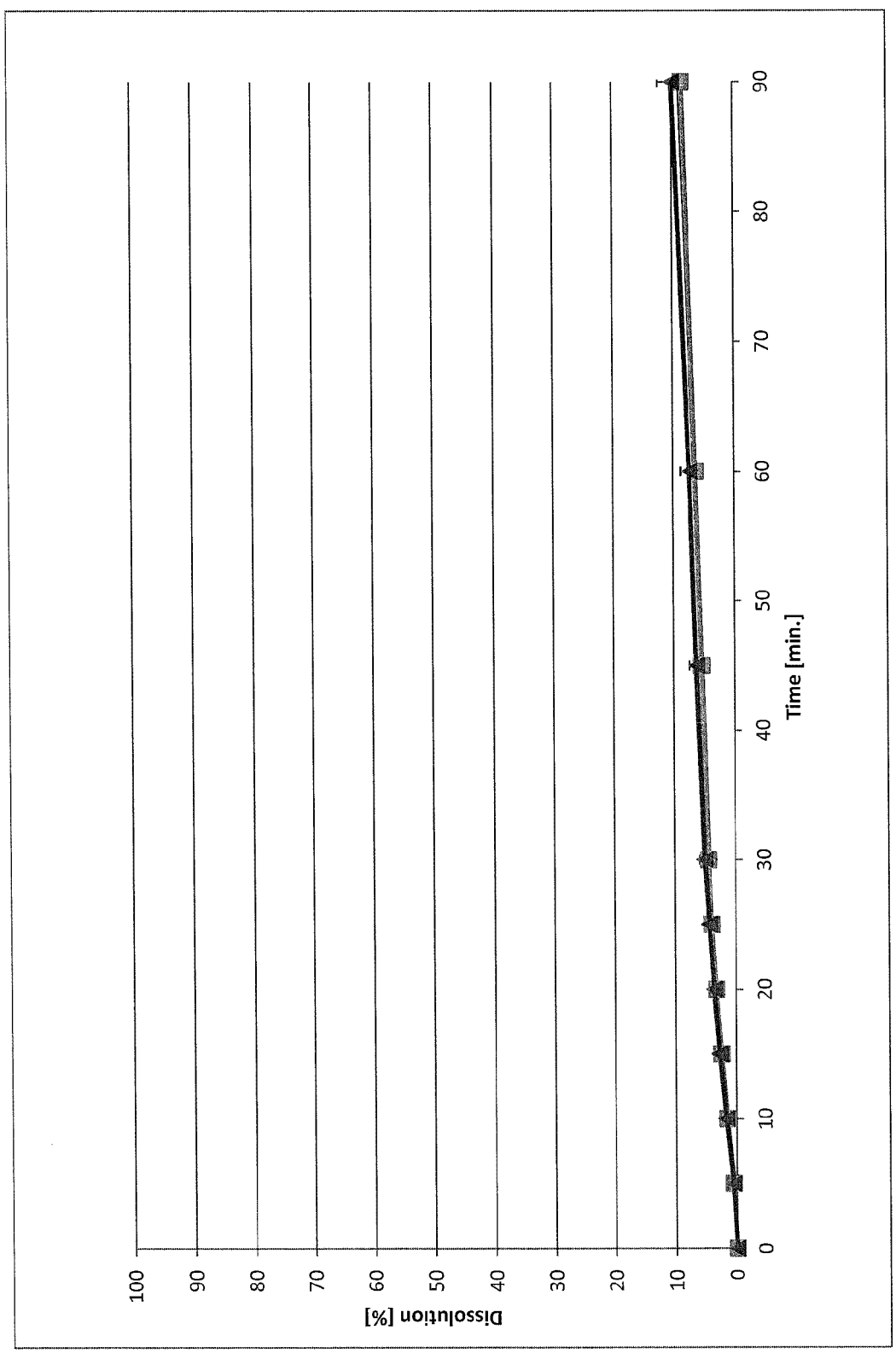
FIG. 8 shows the dissolution profiles of hard gelatin capsules obtained according to example 1 of WO2006/116764 containing 2%, 4% and 6% magnesium stearate, respectively and being obtained according to Comparative Example 1, 2 and 3.

To demonstrate that magnesium stearate has no beneficial effect on the dissolution rate of the active the dissolution profiles of hard gelatine capsules obtained according to example 1 of WO2006/116764 containing 2%, 4% and 6% of magnesium stearate as obtained in comparative examples 1, 2 and 3 were measured according to the above described method. The results of this measurement are shown in FIG. 8. It can be seen that magnesium stearate does not increase the dissolution rate of the active.

Example 13

Figure 9:
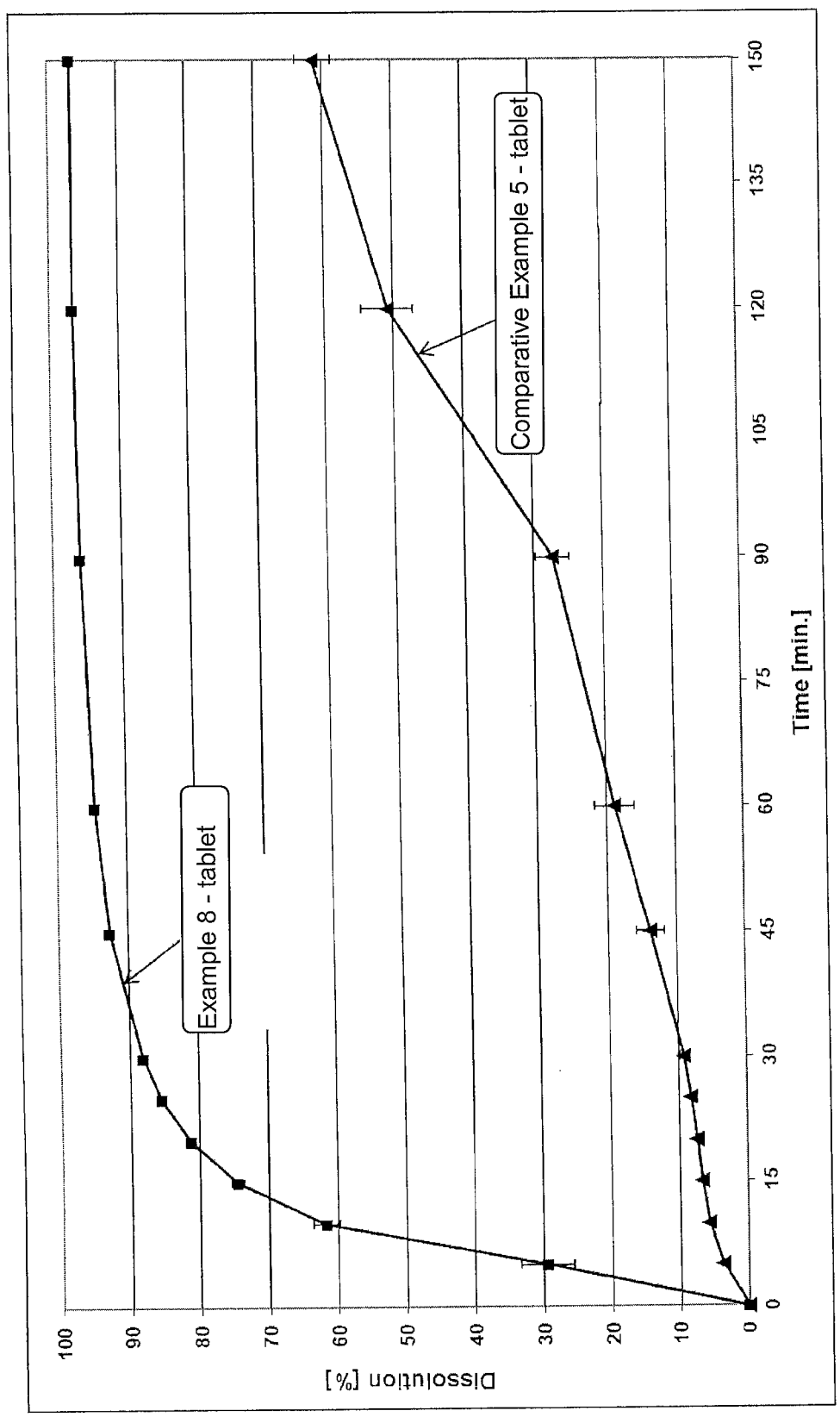
FIG. 9 shows the dissolution profiles of tablets according to the invention (Example 8) and according to Comparative Example 5.
Figure 10:
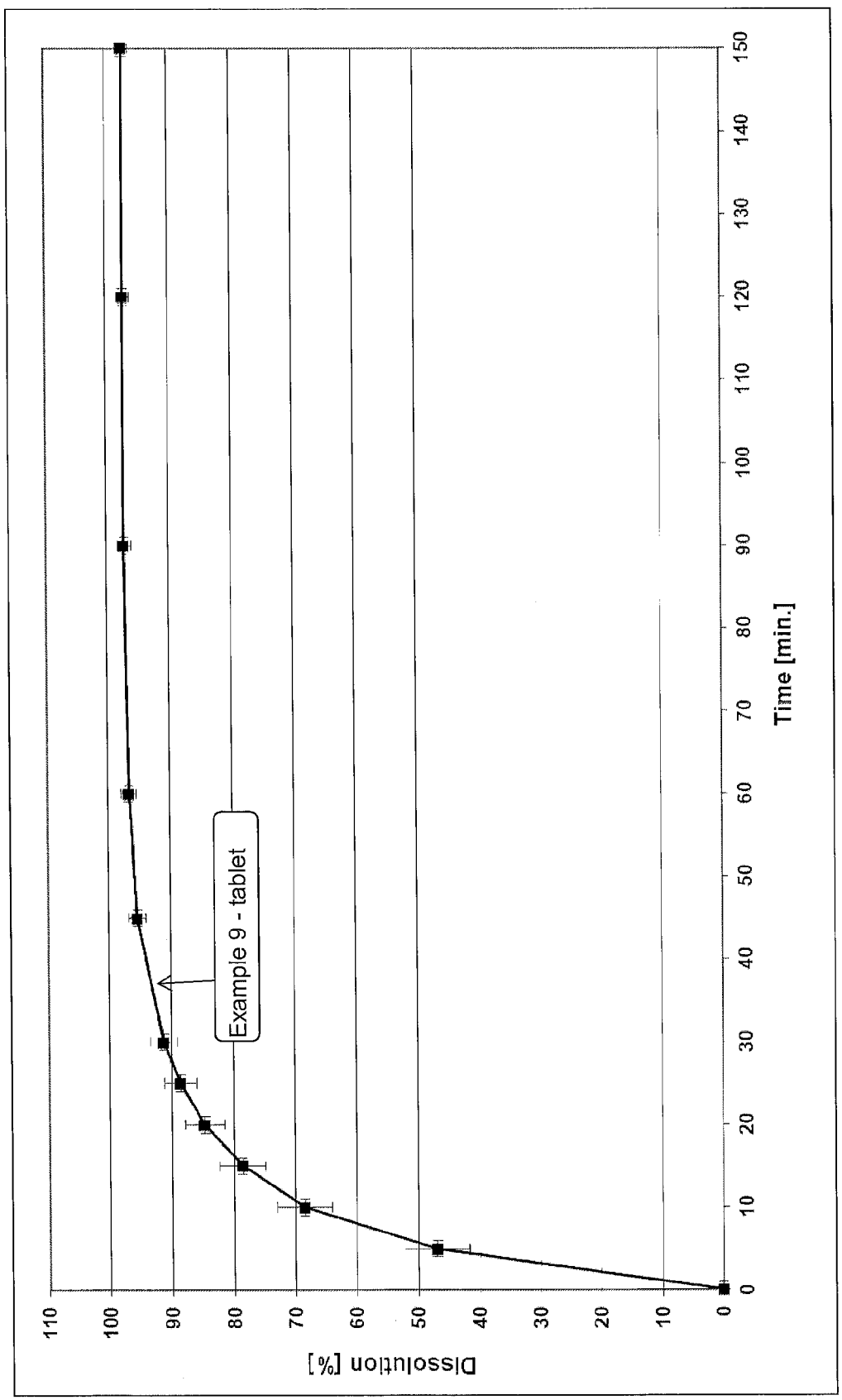
FIG. 10 shows the dissolution profile of tables according to the invention (Example 9)

The dissolution profiles of the tablets obtained in examples 8 and 9 and in comparative example 5 were measured according to the above described method. The results of this measurement are summarized in attached FIGS. 9 and 10. It can be seen that already a low amount of the compound comprising an alkaline earth metal ion is sufficient for significantly increasing the dissolution rate of the active.

Comparative Example 6

Tablets were prepared using the ingredients as summarized in the following table.

TABLE 15

| Compound | Brand ® | amount [mg] | amount [%] |
|---|---|---|---|
| Intragranular phase | | | |
| Dolutegravir sodium | — | 53.24* | 22.18 |
| HPMC | Pharmacoat 603 | 8.00 | 3.33 |
| Sodium lauryl sulphate (SDS) | — | 2.00 | 0.83 |

TABLE 15-continued

| Compound | Brand ® | amount [mg] | amount [%] |
|---|---|---|---|
| Lactose monohydrate | Granulac 200 | 60.00 | 25.00 |
| Microcrystalline cellulose | Avicel PH 101 | 49.76 | 20.73 |
| Croscarmellose sodium | Ac-Di-Sol | 5.00 | 2.08 |
| Extra granular phase | | | |
| Magnesium stearate | — | 2.90 | 1.21 |
| Silicified MCC | Prosolv SMCC 90 | 54.10 | 22.54 |
| Croscarmellose sodium | Ac-Di-Sol | 5.00 | 2.08 |
| TOTAL | | 240.00 | 100.00 |

*adapted to the potency of Dolutegravir sodium

Manufacturing Description

An aqueous solution comprising Pharmacoat 603 was prepared. The active, Granulac 200, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Prosolv and Ac-Di-Sol were added. The mixture was blended for 10 minutes in a Turbula T10B tumble mixer. After addition of Magnesium stearate blending was continued for 3 minutes. Finally, the blend was compressed into tablets on an eccentric press Ek0 with a 9 mm tablet punch.

Figure 11:
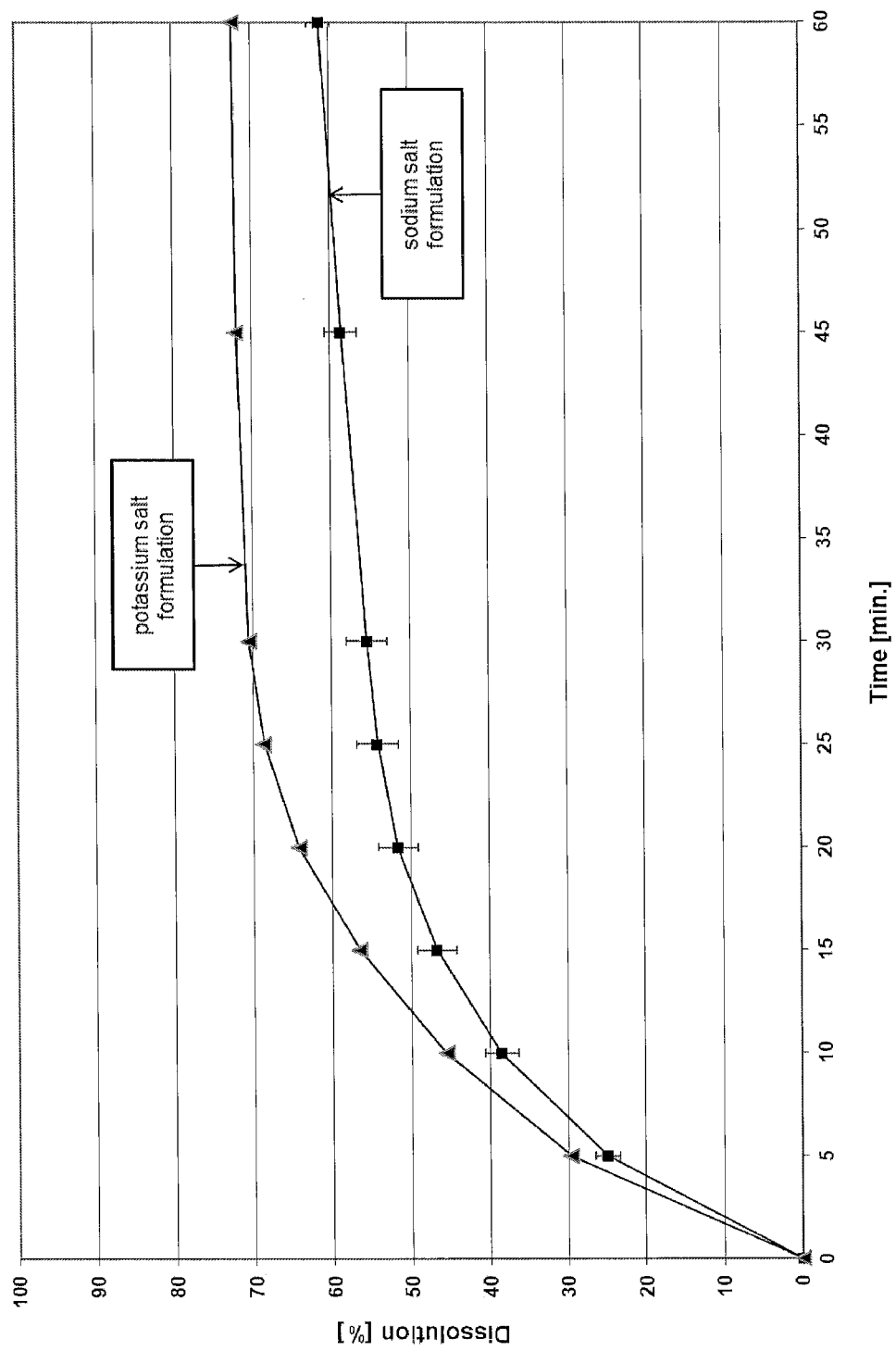
FIG. 11 shows the dissolution profiles of tablets according to Comparative Examples 6 (sodium salt formulation) and 7 (potassium salt formulation)

The dissolution profile of the tablets obtained in this example was measured according to the above described method. The result is shown in FIG. 11.

Comparative Example 7

Tablets were prepared using the ingredients as summarized in the following table.

TABLE 16

| Compound | Brand ® | amount [mg] | amount [%] |
|---|---|---|---|
| Intragranular phase | | | |
| Dolutegravir potassium | — | 56.43* | 23.51 |
| HPMC | Pharmacoat 603 | 8.00 | 3.33 |
| Sodium lauryl sulphate (SDS) | — | 2.00 | 0.83 |
| Lactose monohydrate | Granulac 200 | 60.00 | 25.00 |
| Microcrystalline cellulose | Avicel PH 101 | 50.00 | 20.83 |
| Croscarmellose sodium | Ac-Di-Sol | 5.00 | 2.08 |
| Extra granular phase | | | |
| Magnesium stearate | — | 2.90 | 1.21 |
| Croscarmellose sodium | Ac-Di-Sol | 5.00 | 2.08 |
| Silicified Microcrystalline cellulose | Prosolv SMCC 90 | 50.67 | 21.11 |
| TOTAL | | 240.00 | 100.00 |

*adapted to the potency of Dolutegravir potassium

Manufacturing Description

An aqueous solution comprising Pharmacoat 603 was prepared. Agitation was required in order to achieve complete solution. Dolutegravir potassium, SDS, Granulac 200 and Avicel PH 101 were granulated with the before prepared solution. The obtained granules were sieved through 2000 μm mesh size and subsequently dried at 40° C. After sieving the dried granules through 630 μm mesh size Prosolv SMCC 90 and Ac-Di-Sol were added. The mixture was blended for 10 minutes in a Turbula T10B tumble mixer. After addition of Sodium stearyl fumarate blending was continued for further 3 minutes. Finally, the blend was compressed into tablets on an eccentric press (e.g. Korsch Ek0) with a 9 mm tablet punch.

Figure 12:
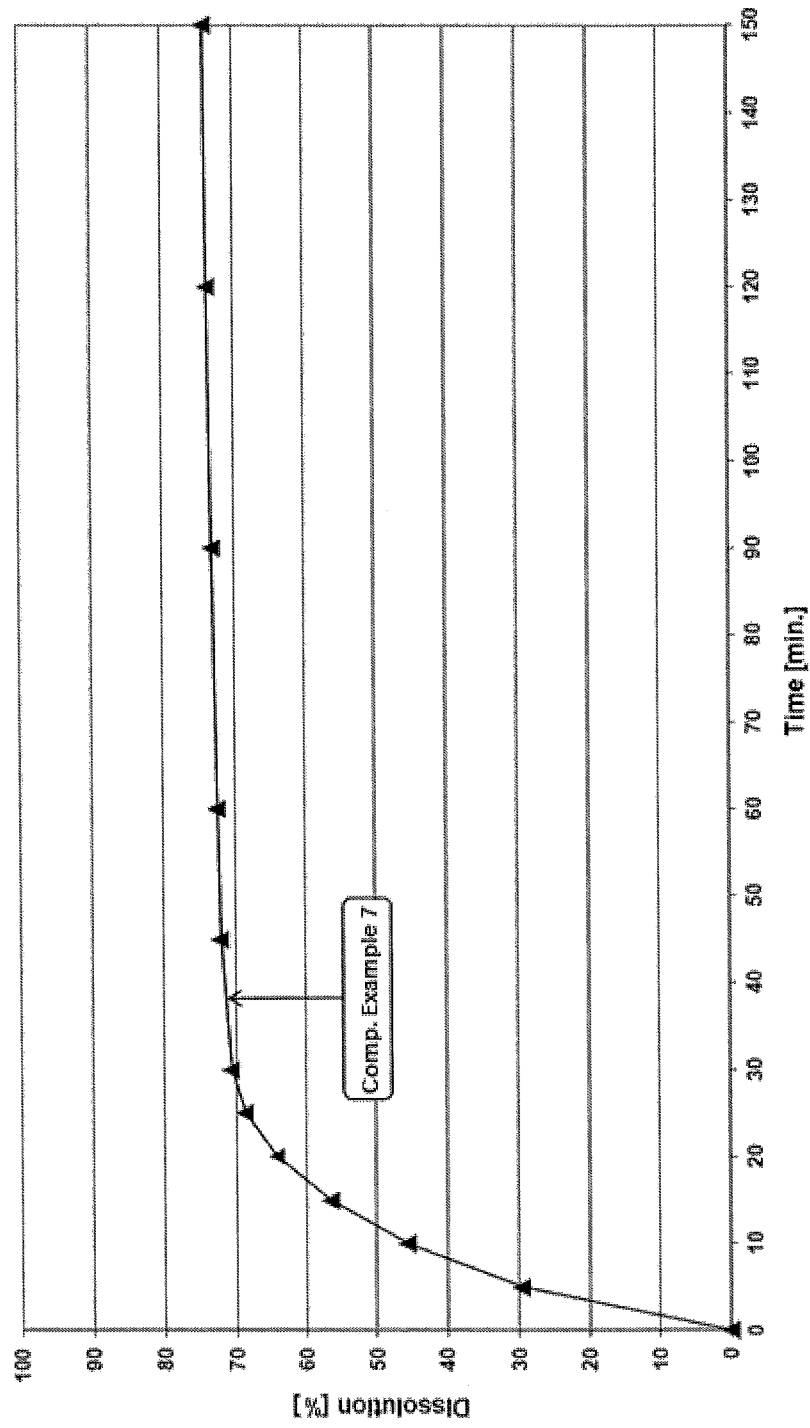
FIG. 12 shows the dissolution profile of tablets according to Comparative Example 7.

The dissolution profile of the tablets obtained in this example was measured according to the above described method. The result is shown in FIGS. 11 and 12.

Example 14

Tablets were prepared using the ingredients as summarized in the following table.

TABLE 17

| Compound | Brand ® | amount [mg] | amount [%] |
|---|---|---|---|
| Intragranular phase | | | |
| Dolutegravir potassium | — | 61.91* | 25.80 |
| HPMC | Pharmacoat 603 | 8.00 | 3.33 |
| Sodium lauryl sulphate (SDS) | — | 2.00 | 0.83 |
| Lactose monohydrate | Granulac 200 | 52.00 | 21.67 |
| Microcrystalline cellulose | Avicel PH 101 | 41.64 | 17.35 |
| Croscarmellose sodium | Ac-Di-Sol | 5.00 | 2.08 |
| Sodium carbonate | — | 11.55 | 4.81 |
| Extra granular phase | | | |
| Magnesium stearate | — | 2.90 | 1.21 |
| Silicified MCC | Prosolv SMCC 90 | 50.00 | 20.83 |
| Croscarmellose sodium | Ac-Di-Sol | 5.00 | 2.08 |
| TOTAL | | 240.00 | 100.00 |

*adapted to the potency of Dolutegravir sodium

Manufacturing Description

An aqueous solution comprising Pharmacoat 603 was prepared. The active, Granulac 200, sodium carbonate, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Prosolv and Ac-Di-Sol were added. The mixture was blended for 10 minutes in a Turbula T10B tumble mixer. After addition of Magnesium stearate blending was continued for 3 minutes. Finally, the blend was compressed into tablets on an eccentric press Ek0 with a 9 mm tablet punch.

Figure 13:
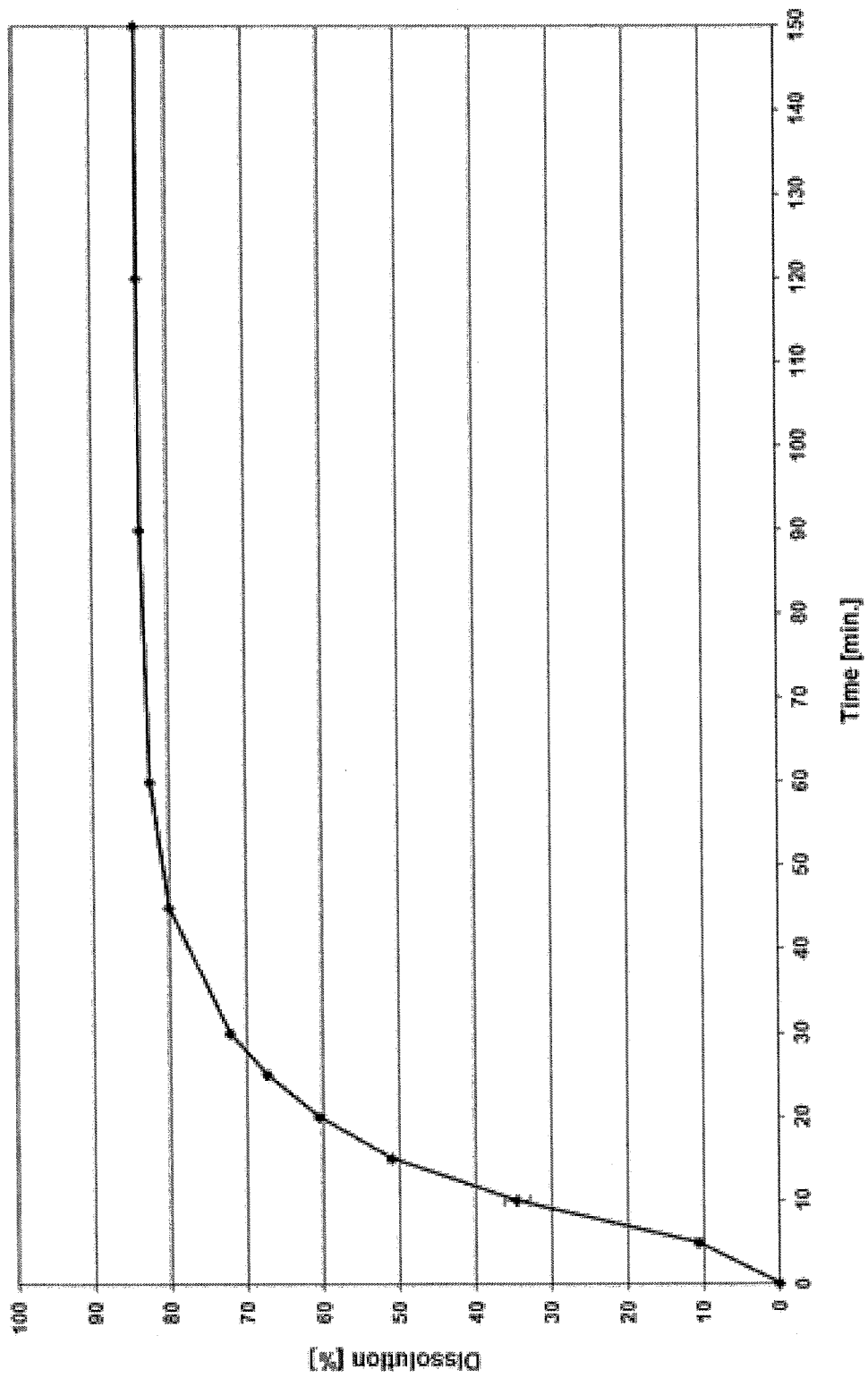
FIG. 13 shows the dissolution profile of tablets according to the invention (Example 14)

The dissolution profile of the tablets obtained in this example was measured according to the above described method. The result is shown in FIG. 13.

Example 15

Tablets were prepared using the ingredients as summarized in the following table.

TABLE 18

| Compound | Brand ® | amount [mg] | amount [%] |
|---|---|---|---|
| Intragranular phase | | | |
| Dolutegravir potassium | — | 61.91* | 25.80 |
| HPMC | Pharmacoat 603 | 8.00 | 3.33 |
| Sodium lauryl sulphate (SDS) | — | 2.00 | 0.83 |
| Lactose monohydrate | Granulac 200 | 42.00 | 17.50 |
| Microcrystalline cellulose | Avicel PH 101 | 31.76 | 13.23 |
| Croscarmellose sodium | Ac-Di-Sol | 5.00 | 2.08 |
| Sodium phosphate | — | 41.43 | 17.26 |

TABLE 18-continued

| Compound | Brand ® | amount [mg] | amount [%] |
|---|---|---|---|
| Extra granular phase | | | |
| Magnesium stearate | — | 2.90 | 1.21 |
| Silicified MCC | Prosolv SMCC 90 | 40.00 | 16.67 |
| Croscarmellose sodium | Ac-Di-Sol | 5.00 | 2.08 |
| TOTAL | | 240.00 | 100.00 |

*adapted to the potency of Dolutegravir sodium

Manufacturing Description

An aqueous solution comprising Pharmacoat 603 was prepared. The active, Granulac 200, sodium phosphate, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Prosolv and Ac-Di-Sol were added. The mixture was blended for 10 minutes in a Turbula T10B tumble mixer. After addition of Magnesium stearate blending was continued for 3 minutes. Finally, the blend was compressed into tablets on an eccentric press Ek0 with a 9 mm tablet punch.

Figure 14:
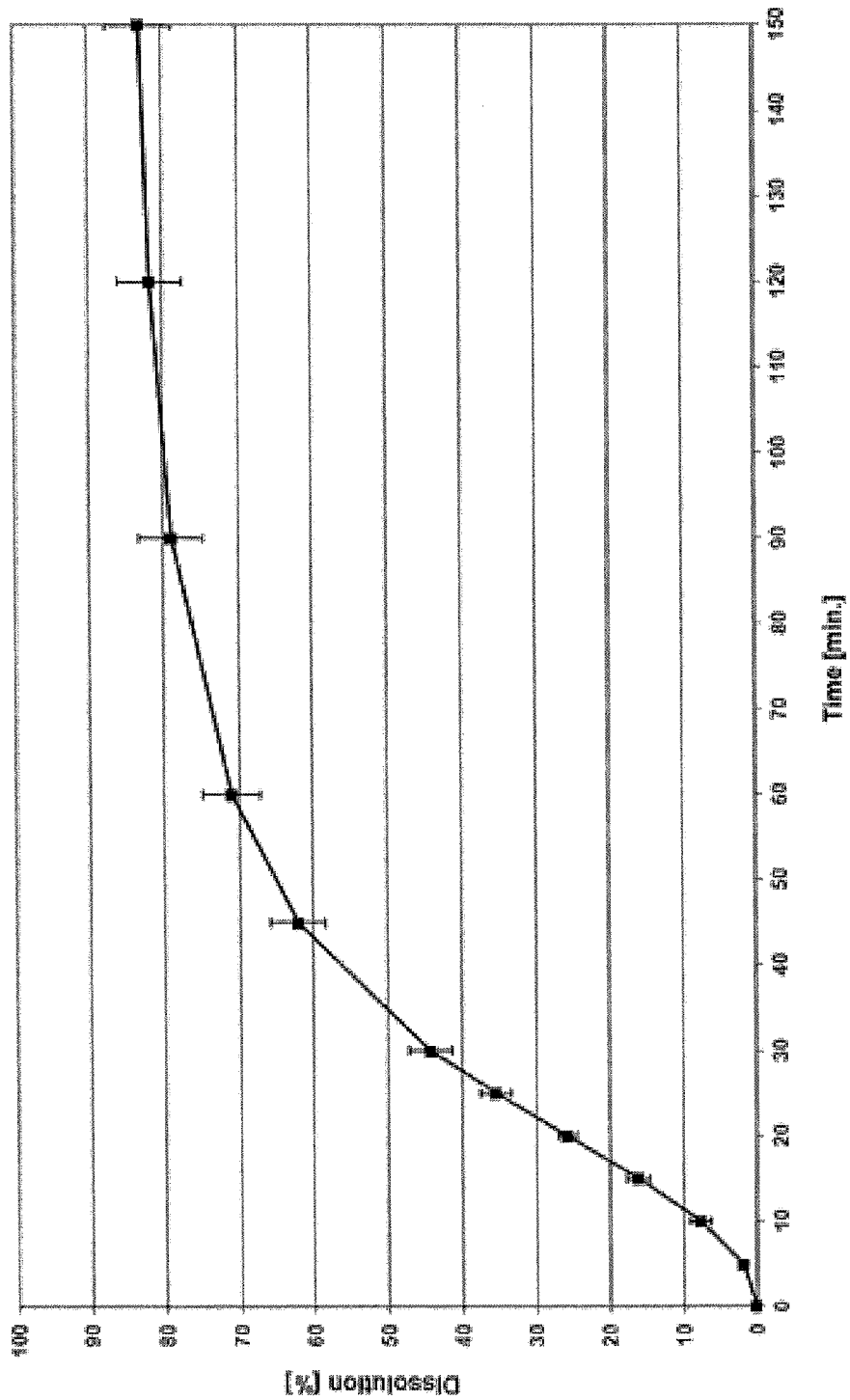
FIG. 14 shows the dissolution profile of tablets according to the invention (Example 15)

The dissolution profile of the tablets obtained in this example was measured according to the above described method. The result is shown in FIG. 14.

Comparative Example 8

Tablets were prepared using the ingredients as summarized in the following table.

TABLE 19

| Compound | Brand ® | amount [mg] | amount [%] |
|---|---|---|---|
| Intragranular phase | | | |
| Dolutegravir potassium | — | 61.91* | 25.80 |
| HPMC | Pharmacoat 603 | 4.00 | 1.67 |
| Sodium lauryl sulphate (SDS) | — | 2.00 | 0.83 |
| Silicified Microcrystalline Cellulose | Prosolv SMCC 90 | 62.09 | 25.87 |
| Sodium starch glycolate | Primojel | 5.00 | 2.08 |
| Extra granular phase | | | |
| Sodium stearyl fumarate | — | 3.00 | 1.25 |
| Sodium starch glycolate | Primojel | 5.00 | 2.08 |
| Silicified Microcrystalline cellulose | Prosolv SMCC 90 | 97.00 | 40.42 |
| TOTAL | | 240.00 | 100.00 |

*adapted to the potency of Dolutegravir sodium

Manufacturing Description

An organic (ethanol-water 1) solution comprising Pharmacoat 603 was prepared. Agitation was required in order to achieve complete solution. Dolutegravir sodium, SDS, Primojel and Prosolv SMCC 90 were granulated with the before prepared solution. The obtained granules were sieved through 2000 μm mesh size and subsequently dried at 40° C. After sieving the dried granules through 630 μm mesh size Prosolv SMCC 90 and Primojel were added. The mixture was blended for 10 minutes in a Turbula T10B tumble mixer. After addition of Sodium stearyl fumarate blending was continued for further 3 minutes. Finally, the blend was compressed into tablets on an eccentric press (e.g. Korsch Ek0) with a 9 mm tablet punch.

Figure 15:
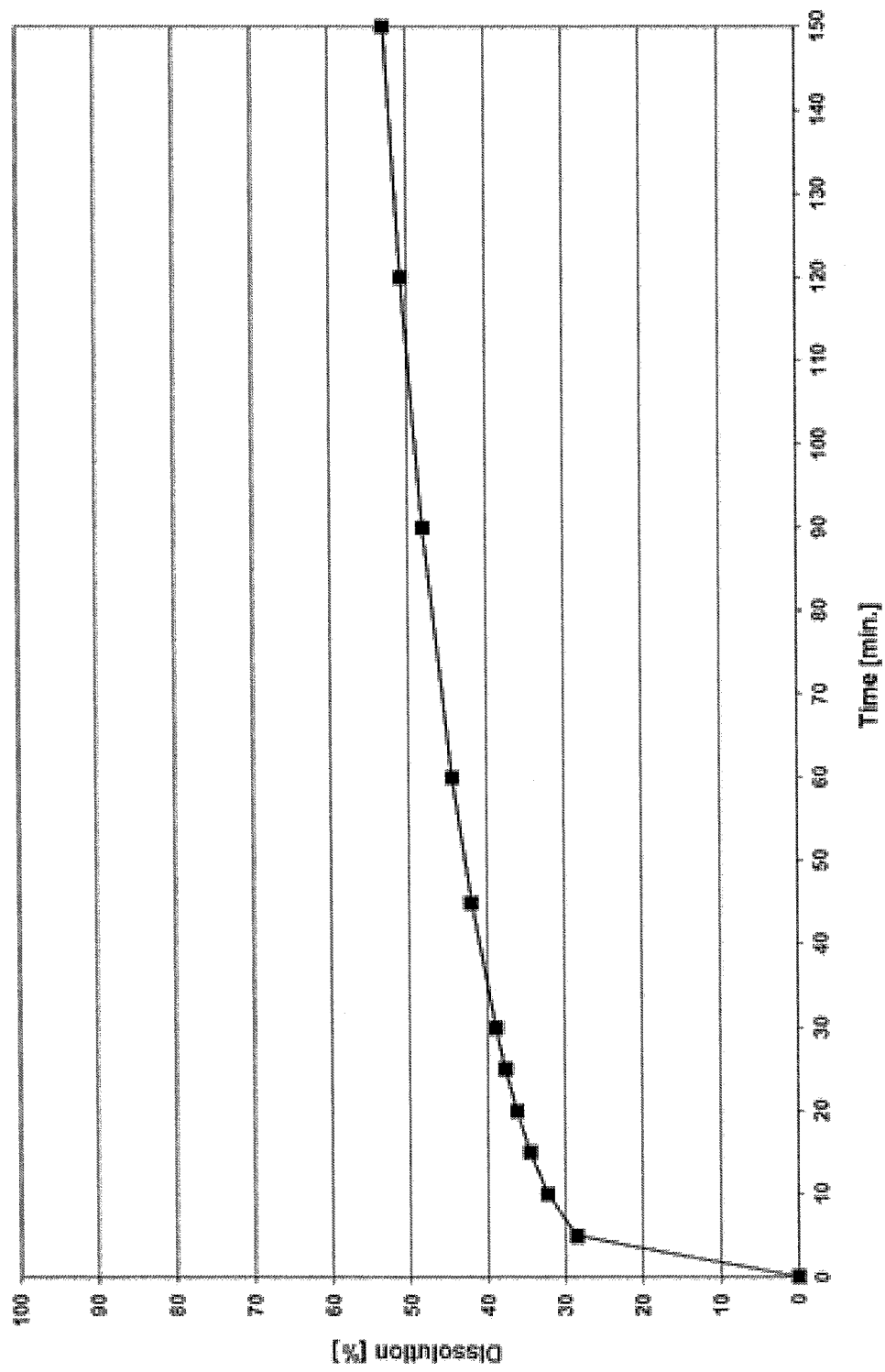
FIG. 15 shows the dissolution profile of tablets according to Comparative Example 8.

The dissolution profile of the tablets obtained in this example was measured according to the above described method. The result is shown in FIG. 15.

Example 16

Tablets were prepared using the ingredients as summarized in the following table.

TABLE 20

| Compound | Brand ® | amount [mg] | amount [%] |
|---|---|---|---|
| Intragranular phase | | | |
| Dolutegravir sodium | — | 53.24* | 22.18 |
| HPMC | Pharmacoat 603 | 4.00 | 1.67 |
| Sodium lauryl sulphate (SDS) | — | 2.00 | 0.83 |
| Silicified Microcrystalline Cellulose | Prosolv SMCC 90 | 46.28 | 19.28 |
| Sodium starch glycolate | Primojel | 5.00 | 2.08 |
| Trisodium phosphate | — | 21.48 | 8.95 |
| Extra granular phase | | | |
| Sodium stearyl fumarate | — | 3.00 | 1.25 |
| Sodium starch glycolate | Primojel | 5.00 | 2.08 |
| Silicified Microcrystalline cellulose | Prosolv SMCC 90 | 100.00 | 41.67 |
| TOTAL | | 240.00 | 100.00 |

*adapted to the potency of Dolutegravir sodium

Manufacturing Description

An organic solution comprising Pharmacoat 603 was prepared. Agitation was required in order to achieve complete solution. Dolutegravir sodium, $Na_3PO_4$, SDS, Primojel and Prosolv SMCC 90 were granulated with the before prepared solution. The obtained granules were sieved through 2000 μm mesh size and subsequently dried at 40° C. After sieving the dried granules through 630 μm mesh size Prosolv SMCC 90 and Primojel were added. The mixture was blended for 10 minutes in a Turbula T10B tumble mixer. After addition of Sodium stearyl fumarate blending was continued for further 3 minutes. Finally, the blend was compressed into tablets on an eccentric press (e.g. Korsch Ek0) with a 9 mm tablet punch.

Figure 16:
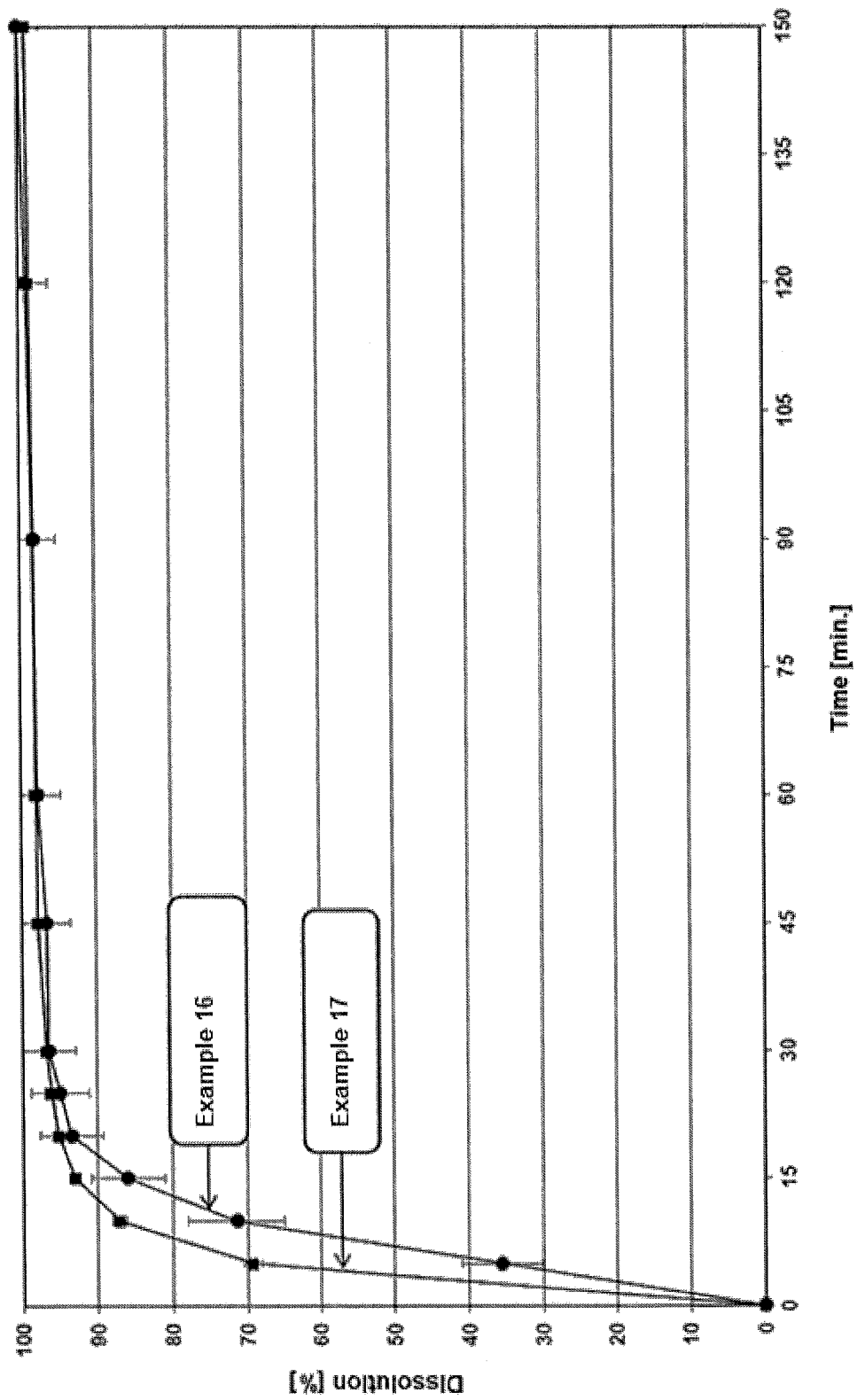
FIG. 16 shows the dissolution profiles of tablets according to the invention (Examples 16 and 17)

The dissolution profile of the tablets obtained in this example was measured according to the above described method. The result is shown in FIG. 16.

Example 17

Tablets were prepared using the ingredients as summarized in the following table.

TABLE 21

| Compound | Brand ® | amount [mg] | amount [%] |
|---|---|---|---|
| Intragranular phase | | | |
| Dolutegravir sodium | — | 53.24* | 22.18 |
| HPMC | Pharmacoat 603 | 4.00 | 1.67 |
| Sodium lauryl sulphate (SDS) | — | 2.00 | 0.83 |
| Silicified Microcrystalline Cellulose | Prosolv SMCC 90 | 22.81 | 9.50 |
| Sodium starch glycolate | Primojel | 5.00 | 2.08 |
| Trisodium phosphate | — | 42.95 | 17.90 |

TABLE 21-continued

| Compound | Brand ® | amount [mg] | amount [%] |
|---|---|---|---|
| Extra granular phase | | | |
| Sodium stearyl fumarate | — | 3.00 | 1.25 |
| Sodium starch glycolate | Primojel | 5.00 | 2.08 |
| Silicified Microcrystalline cellulose | Prosolv SMCC 90 | 102.00 | 42.50 |
| | TOTAL | 240.00 | 100.00 |

*adapted to the potency of Dolutegravir sodium

Manufacturing Description

An organic solution comprising Pharmacoat 603 was prepared. Agitation was required in order to achieve complete solution. Dolutegravir sodium, $Na_3PO_4$, SDS, Primojel and Prosolv SMCC 90 were granulated with the before prepared solution. The obtained granules were sieved through 2000 μm mesh size and subsequently dried at 40° C. After sieving the dried granules through 630 μm mesh size Prosolv SMCC 90 and Primojel were added. The mixture was blended for 10 minutes in a Turbula T10B tumble mixer. After of Sodium stearyl fumarate blending was continued for further 3 minutes. Finally, the blend was compressed into tablets on an eccentric press (e.g. Korsch Ek0) with a 9 mm tablet punch.

The dissolution profile of the tablets obtained in this example was measured according to the above described method. The result is shown in FIG. 16.

Example 18

Tablets were prepared using the ingredients as summarized in the following table.

TABLE 22

| Compound | Brand ® | amount [mg] | amount [%] |
|---|---|---|---|
| Intragranular phase | | | |
| Dolutegravir potassium | — | 61.91* | 25.80 |
| HPMC | Pharmacoat 603 | 4.00 | 1.67 |
| Sodium lauryl sulphate (SDS) | — | 2.00 | 0.83 |
| Silicified Microcrystalline Cellulose | Prosolv SMCC 90 | 41.73 | 17.39 |
| Sodium starch glycolate | Primojel | 5.00 | 2.08 |
| Tripotassium citrate | — | 35.36 | 14.73 |
| Extra granular phase | | | |
| Sodium stearyl fumarate | — | 3.00 | 1.25 |
| Sodium starch glycolate | Primojel | 5.00 | 2.08 |
| Silicified Microcrystalline cellulose | Prosolv SMCC 90 | 82.00 | 34.17 |
| | TOTAL | 240.00 | 100.00 |

*adapted to the potency of Dolutegravir sodium

Manufacturing Description

An organic solution comprising Pharmacoat 603 was prepared. Agitation was required in order to achieve complete solution. Dolutegravir sodium, SDS, Tripotassium citrate, Primojel and Prosolv SMCC 90 were granulated with the before prepared solution. The obtained granules were sieved through 2000 μm mesh size and subsequently dried at 40° C. After sieving the dried granules through 630 μm mesh size Prosolv SMCC 90 and Primojel were added. The mixture was blended for 10 minutes in a Turbula T10B tumble mixer. After addition of Sodium stearyl fumarate blending was continued for further 3 minutes. Finally, the blend was compressed into tablets on an eccentric press (e.g. Korsch Ek0) with a 9 mm tablet punch.

Figure 17:
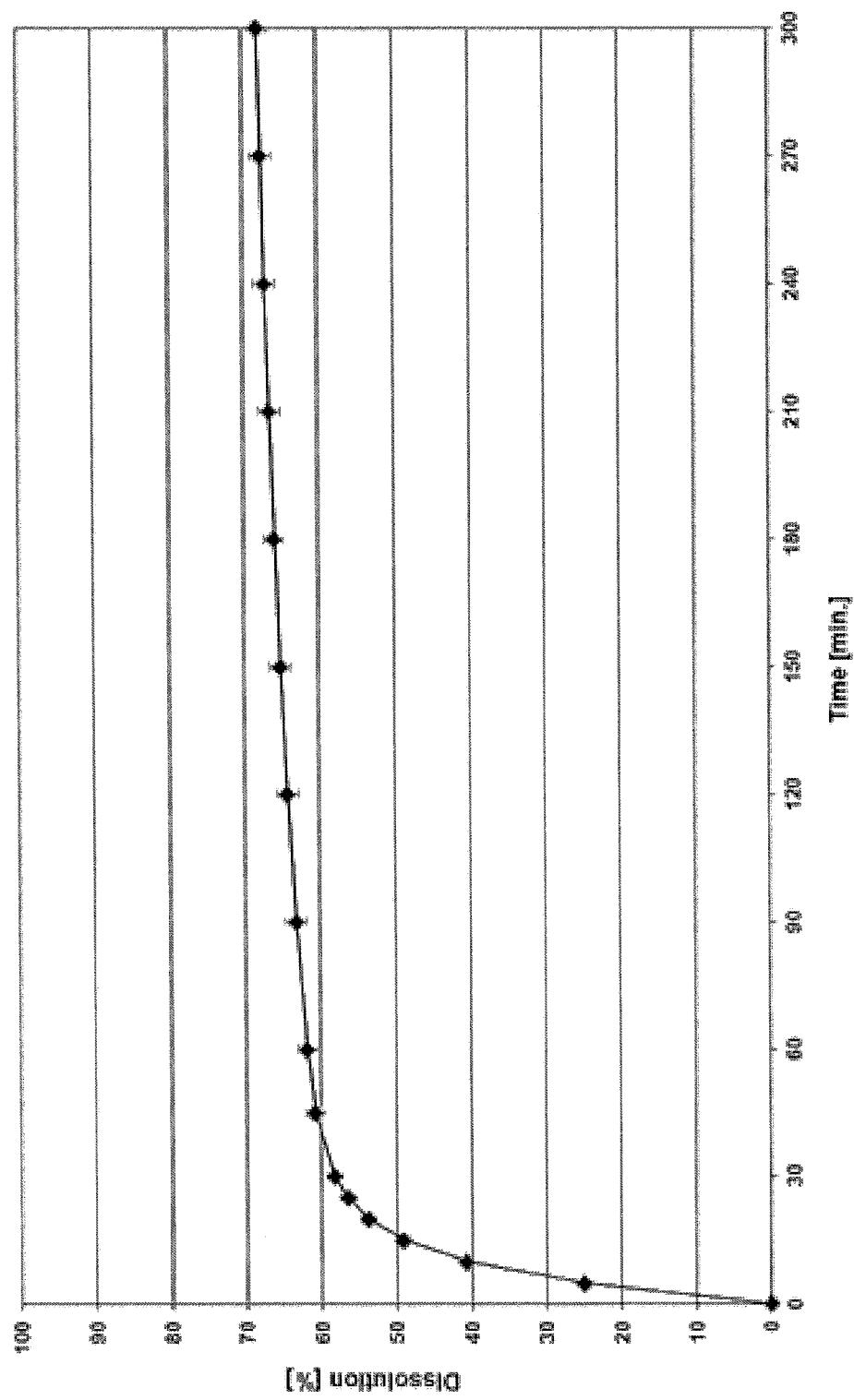
FIG. 17 shows the dissolution profile of tablets according to the invention (Example 18)

The dissolution profile of the tablets obtained in this example was measured according to the above described method. The result is shown in FIG. 17.

Example 19

Tablets were prepared using the ingredients as summarized in the following table.

TABLE 23

| Compound | Brand ® | amount [mg] | amount [%] |
|---|---|---|---|
| Intragranular phase | | | |
| Dolutegravir sodium | — | 53.24* | 22.18 |
| HPMC | Pharmacoat 603 | 4.00 | 1.67 |
| Sodium lauryl sulphate (SDS) | — | 2.00 | 0.83 |
| Silicified Microcrystalline Cellulose | Prosolv SMCC 90 | 52.53 | 21.89 |
| Sodium starch glycolate | Primojel | 5.00 | 2.08 |
| Trisodium citrate | — | 33.23 | 13.85 |
| Extra granular phase | | | |
| Sodium stearyl fumarate | — | 3.00 | 1.25 |
| Sodium starch glycolate | Primojel | 5.00 | 2.08 |
| Silicified Microcrystalline cellulose | Prosolv SMCC 90 | 82.00 | 34.17 |
| | TOTAL | 240.00 | 100.00 |

*adapted to the potency of Dolutegravir sodium

Manufacturing Description

An organic solution comprising Pharmacoat 603 was prepared. Agitation was required in order to achieve complete solution. Dolutegravir sodium, SDS, Trisodium citrate, Primojel and Prosolv SMCC 90 were granulated with the before prepared solution. The obtained granules were sieved through 2000 μm mesh size and subsequently dried at 40° C. After sieving the dried granules through 630 μm mesh size Prosolv SMCC 90 and Primojel were added. The mixture was blended for 10 minutes in a Turbula T10B tumble mixer. After addition of Sodium stearyl fumarate blending was continued for further 3 minutes. Finally, the blend was compressed into tablets on an eccentric press (e.g. Korsch Ek0) with a 9 mm tablet punch.

Figure 18:
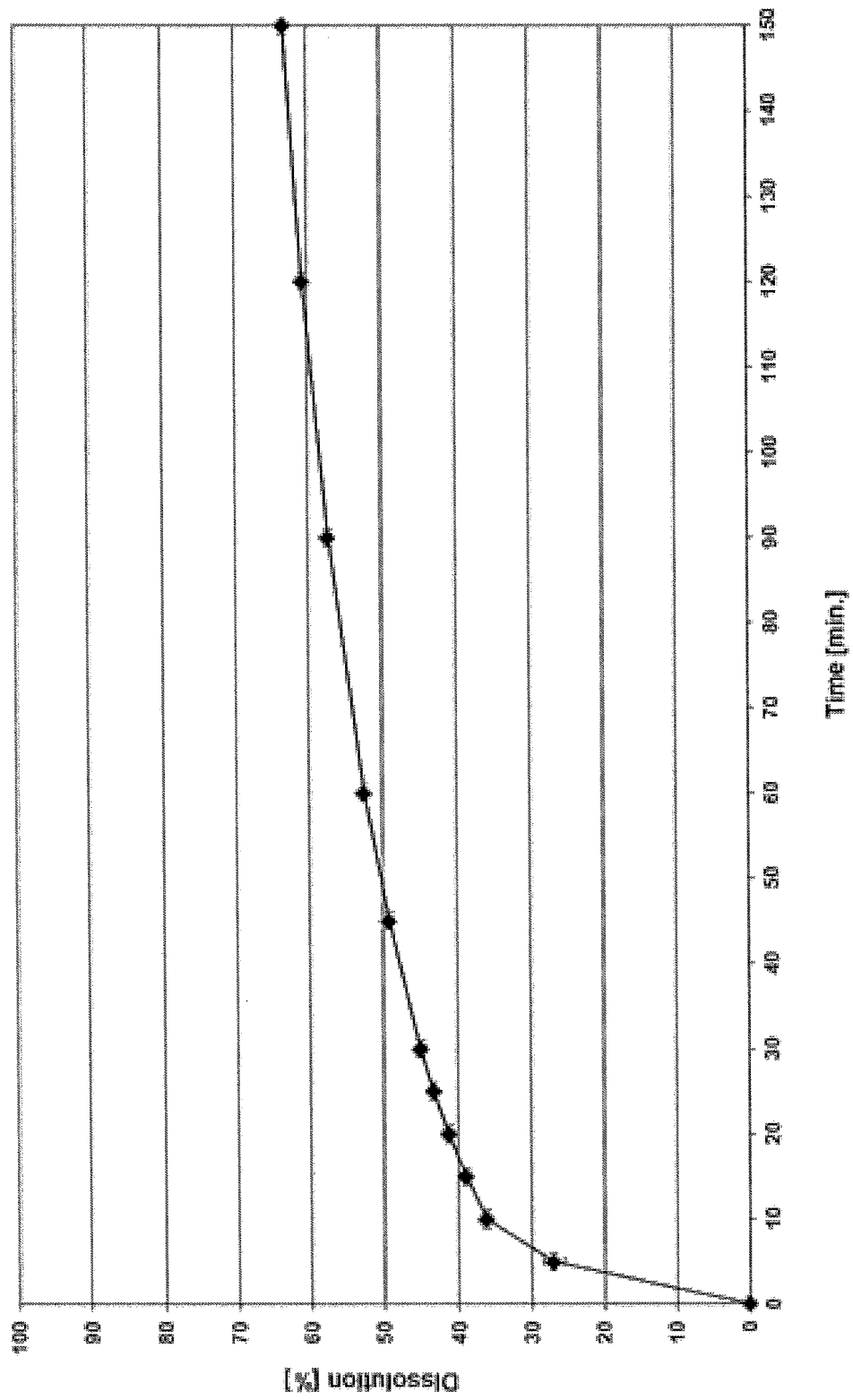
FIG. 18 shows the dissolution profile of tablets according to the invention (Example 19)

The dissolution profile of the tablets obtained in this example was measured according to the above described method. The result is shown in FIG. 18.

The invention claimed is:

1. A solid pharmaceutical dosage form comprising dolutegravir or a pharmaceutically acceptable salt or solvate thereof in combination with an alkaline compound selected from the group consisting of sodium carbonate, calcium carbonate, and magnesium oxide.

2. The solid pharmaceutical dosage form according to claim 1, wherein said dolutegravir or a pharmaceutically acceptable salt or solvate thereof and said alkaline compound are present in a molar ratio ranging from 1:10 to 10:1.

3. The solid pharmaceutical dosage form according to claim 1, wherein said dosage form contains from 0.5 to 15% by weight of the alkaline compound based on the total weight of the dosage form.

4. The solid pharmaceutical dosage form according to claim 1, wherein said dosage form further comprises one or more further pharmaceutically acceptable excipients.

5. The solid pharmaceutical dosage form according to claim 4, wherein said dosage form further comprises at least one disintegrant.

6. The solid pharmaceutical dosage form according to claim 1, wherein said dosage form is in the form of a capsule or tablet.

7. The solid pharmaceutical dosage form according to claim 6, wherein said dosage form is obtained by wet granulation.

8. The solid pharmaceutical dosage form according to claim 1, wherein at least 10% of the total amount of the dolutegravir or pharmaceutically acceptable salt or solvate thereof present in the dosage form is dissolved in less than 10 minutes when measured using USP paddle Apparatus II in 900 ml 0.1 N HCl, pH 1.2, at 37° C. and 100 rpm.

9. The solid pharmaceutical dosage form according to claim 8, wherein at least 70% of the total amount of dolutegravir or pharmaceutically acceptable salt or solvate thereof present in the dosage form is dissolved in less than 20 minutes when measured using USP paddle Apparatus II in 900 ml 0.1 N HCl, pH 1.2, at 37° C. and 100 rpm.

10. The solid pharmaceutical dosage form according to claim 1, wherein said dolutegravir is present as dolutegravir sodium salt.

\* \* \* \* \*